(12) United States Patent
Isobe et al.

(10) Patent No.: US 6,376,501 B1
(45) Date of Patent: Apr. 23, 2002

(54) TYPE 2 HELPER T CELL-SELECTIVE IMMUNE RESPONSE SUPPRESSORS

(75) Inventors: Yoshiaki Isobe; Haruhisa Ogita; Masanori Tobe; Haruo Takaku; Hiroyuki Matsui; Hideyuki Tomizawa, all of Saitama (JP)

(73) Assignee: Japan Energy Corporation, Tokyo (JP)

( * ) Notice: Subject to any disclaimer, the term of this patent is extended or adjusted under 35 U.S.C. 154(b) by 0 days.

(21) Appl. No.: 09/582,176

(22) PCT Filed: Dec. 21, 1998

(86) PCT No.: PCT/JP98/05779

§ 371 Date: Jun. 21, 2000

§ 102(e) Date: Jun. 21, 2000

(87) PCT Pub. No.: WO99/32122

PCT Pub. Date: Jul. 1, 1999

(51) Int. Cl.⁷ .............................................. A61K 31/52
(52) U.S. Cl. ....................................................... 514/262
(58) Field of Search ......................................... 514/262

(56) References Cited

U.S. PATENT DOCUMENTS 6,028,076 A * 2/2000 Hirota et al.

FOREIGN PATENT DOCUMENTS

| EP | 0 778 277 | 6/1997 |
|---|---|---|
| JP | 4-503506 | 6/1992 |
| JP | 9-188682 | 7/1997 |
| WO | WO90/09178 | 8/1990 |
| WO | WO98/01448 | 1/1998 |

OTHER PUBLICATIONS

Kelley J.L. et al., Benzodiazepine Receptor Binding Activity of 8–Substituted–9–(3–substituted–benzyl)–6–(dimethylamino)–9 H,–purines, J.Med. Chem., vol.33, pp. 196–202 (1990).

De Clercq E. et al., Antiviral Activity of Aliphatic Nucleoside Analogues: Structure–Function Relationship, J. Med. Chem., vol, No. 5, pp. 510–513 (1979).

Holy A. et al., Structure–Activity Studies On Open Chain Analogues Of Nucleosides: Inhibition Of S–Adenosyl–$^L$––Homocysteine Hydrolase And Antiviral Activity 1. Neutral Open–Chain Analogues, collection Czechoslovak Chem. Commun., vol. 50, pp. 245–261 (1985).

* cited by examiner

Primary Examiner—William R. A. Jarvis
(74) Attorney, Agent, or Firm—Fish & Richardson P.C.

(57) ABSTRACT

The present invention relates to a type 2 helper T cell-selective immune response inhibitor, an immune response regulator and an anti-allergic agent, individually comprising, as an active ingredient, a purine derivative represented by General Formula (I):

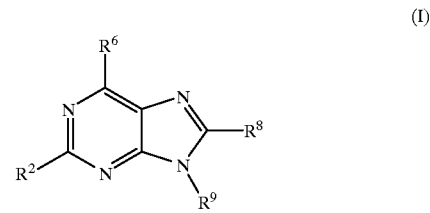

(I)

wherein $R^2$ is hydrogen or a hydrocarbon group in which —$CH_2$— not directly bound to the purine skeleton may be substituted by CO, $SO_2$, O or S, and C—H not directly bound to the purine skeleton may be substituted by N, C-halogen or C—CN;

$R^6$ is hydroxyl, amino or amino which is mono- or di-substituted by a hydrocarbon group(s);

$R^8$ is hydroxyl, mercapto, acyloxy or hydrocarbon group-substituting oxycarbonyloxy; and $R^9$ is a hydrocarbon group in which —$CH_2$— not directly bound to the purine skeleton may be substituted by CO, $SO_2$, O or S, and C—H not directly bound to the purine skeleton may be substituted by N, C-halogen or C—CN;

or its tautomer or a salt of the purine derivative or the tautomer.

6 Claims, No Drawings

TYPE 2 HELPER T CELL-SELECTIVE IMMUNE RESPONSE SUPPRESSORS

This application is a 371 of PCT/JP98/05779, filed Dec. 21, 1998.

TECHNICAL FIELD

The present invention generally relates to pharmaceutical compositions comprising as an active ingredient a compound having purine structure, and specifically relates to a type 2 helper T cell (hereinafter abbreviated to "Th2")-selective immune response inhibitor and an immune response regulator. More specifically, the present invention relates to a Th2-selective immune response inhibitor and an immune response regulator which can effectively treat or prevent those diseases attributable to abnormal rise immunize response on the Th2 side (i.e. allergic diseases such as asthma, allergic dermatitis or allergic rhinitis, or autoimmune diseases such as systemic lupus erythematosus) by inhibiting immune response on the Th2 side and enhancing immune response on the type 1 helper T cell (hereinafter abbreviated to "Th1") side.

BACKGROUND ART

What is playing the major role in immune response is helper T cells. There are two classes, Th1 and Th2, in helper T cells. Cytokines produced when Th1 is activated include interleukin-2 (IL-2) and interferon-γ (IFN-γ); and cytokines produced when Th2 is activated include interleukin-4 (IL-4) and interleukin-5 (IL-5). Cytokines on the Th1 side induce activation of macrophages and natural killer cells, and are mainly involved in cellular immunity such as infection control against viruses and bacteria. On the other hand, it is known that cytokines on the Th2 side are involved in humoral immunity such as antibody production from B cells. Particularly, IL- 4 not only induces production of IgE antibody by B cells, but also has an action of differentiating and proliferating Th2 cells. IL-5 has various actions such as activation, differentiation/proliferation and lifetime prolongation of eosinophils, and plays an important role in allergic inflammation. Thus, it is considered that allergic inflammation is caused by abnormal rise in immune response on the Th2 side. Actually, the presence of IL-4 and IL-5 has been confirmed in affected parts of asthma patients and patients with atopic dermatitis.

Conventionally, asthma, atopic dermatitis and the like have been treated with anti-allergic agents. However, such agents do not inhibit the immune response by Th2; as in the case of histamine, they only inhibit a part of allergic reactions in the downstream. Thus, their clinical effect is insufficient. Consequently, only steroids have been proved effective against these diseases. However, long term administration of steroids causes wide-ranging side effects (diabetes, infections, adrenal dysfunction, moon face, etc.). Since steroids inhibit immune response on both the Th1 side and the Th2 side, administration of steroids results in the lowering of patients' resistance to viral infections as their immune response is lowered. In order to overcome this drawback, a drug which inhibits immune response on the Th2 side and simultaneously enhances immune response on the Th1 side can be said more preferable since such a drug has an advantage of preventing infections caused by virus or the like.

From what has been described so far, it is considered that if a drug which enhances immune response on the Th1 side represented by production of IFN-γ and inhibits immune response on the Th2 side represented by production of IL-4 and IL-5 is developed, the drug will be an effective and highly safe therapeutic or prophylactic for allergic diseases Autoimmune diseases such as systemic lupus erythematosus are also presumed to be a state in which immune response on the Th2 side has been abnormally exasperated (Medical Immunology, 15, 401, 1985). Thus, a drug which enhances immune response on the Th1 side and inhibits immune response on the Th2 side as described above is expected to be a therapeutic for autoimmune diseases.

DISCLOSURE OF THE INVENTION

Under such circumstances, it is an object of the present invention to provide an effective therapeutic for allergic diseases caused by abnormal rise in immune response on the Th2 side, which therapeutic treats allergic diseases by enhancing immune response on the Th1 side represented by production of IFN-γ, etc. and simultaneously inhibiting immune response on the Th2 side represented by production of IL-4, IL-5, etc.

As a result of extensive and intensive researches to develop a drug which enhances immune response on the Th1 side represented by production of IFN-γ, etc. and simultaneously inhibits immune response on the Th2 side represented by production of IL-4, IL-5, etc., the prevent inventors have found that purine derivatives having a specific structure enhance immune response on the Th1 side and inhibit immune response on the Th2 side. Thus, the present invention has been achieved.

The present invention relates to a type 2 helper T cell-selective immune response inhibitor and an immune response regulator, individually comprising, as an active ingredient, a purine derivative represented by General Formula (I):

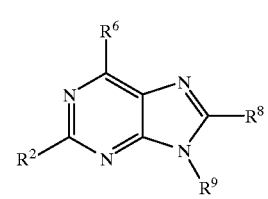

(I)

wherein
R² is hydrogen or a C₁₋₁₄ hydrocarbon group in which
—CH₂— not directly bound to the purine skeleton and CH₂ in —CH₃ not directly bound to the purine skeleton may be substituted by carbonyl, sulfonyl, —O— or —S—; =CH₂ may be substituted by =O or =S; C—H in —CH₂— not directly bound to the purine skeleton, C—H in —CH₃ not directly bound to the purine skeleton, C—H in >CH— not directly bound to the purine skeleton, C—H in =CH— not directly bound to the purine skeleton and C—H in =CH₂ may be substituted by N, C-halogen or C—CN;

R⁶ is hydroxyl, amino or amino which is mono- or di-substituted by a C₁₋₁₀ hydrocarbon group(s);

R⁸ is hydroxyl, mercapto, C₁₋₁₈ acyloxy or C₁₋₁₉ hydrocarbon group-substituting oxycarbonyloxy; and R⁹ is a C₁₋₁₄ hydrocarbon group in which —CH₂— not directly bound to the purine skeleton and CH₂ in —CH₃ not directly bound to the purine skeleton may be substituted by carbonyl, sulfonyl, —O— or —S—; =CH₂ may be substituted by =O or =S; C—H in —CH$_2$— not directly bound to the purine skeleton, C—H in —CH$_3$ not directly bound to the purine skeleton, C—H in >CH— not directly bound to the purine skeleton, C—H in =CH— not directly bound to the purine skeleton, C—H in =CH$_2$ and C—H in ≡CH may be substituted by N, C-halogen or C—CN; or its tautomer or a pharmaceutically acceptable salt of the purine derivative or the tautomer.

Specifically, the Th2-selective immune response inhibitor and the immune response regulator of the invention are used as an anti-allergic agent; they are pharmaceuticals to be administered for alleviating the conditions of allergic diseases developed by various causes or for preventing the manifestation of symptoms. Specifically, the above-mentioned allergic diseases include allergic dermatitis, allergic rhinitis, atopic dermatitis, asthma (atopic asthma, non-atopic asthma) and the like. The Th2-selective immune response inhibitor and the immune response regulator of the invention are used as a therapeutic or prophylactic for such diseases. Furthermore, they are used as a therapeutic or prophylactic for autoimmune diseases such as systemic lupus erythematosus having similar uncomfortable symptoms.

Hereinbelow, the purine derivative represented by General Formula (I) which is used as an active ingredient in the present invention will be described in more detail.

First, the hydrocarbon group in General Formula (I) described above includes any of straight- or branched-chain hydrocarbon groups; monocyclic hydrocarbon groups without or with a side chain(s); polycyclic hydrocarbon groups without or with a side chain(s); spiro hydrocarbon groups without or with a side chain(s); ring-assembling structural hydrocarbon groups without or with a side chain(s); or chain hydrocarbon groups substituted by the above-described cyclic hydrocarbon group(s). The hydrocarbon group in General Formula (I) also includes both saturated hydrocarbon groups and unsaturated hydrocarbon groups, but it does not include those unsaturated hydrocarbon groups which have the ketine structure C=C=C. Specific examples of straight- or branched-chain hydrocarbon groups include straight-chain alkyl with 1 or more carbon atoms, branched-chain alkyl with 3 or more carbon atoms (which are saturated chain hydrocarbon groups); straight-chain alkenyl with 2 or more carbon atoms, branched-chain alkenyl with 3 or more carbon atoms, straight-chain alkynyl with 3 or more carbon atoms, branched-chain alkynyl with 4 or more carbon atoms, straight-chain alkadienyl with 4 or more carbon atoms, and branched-chain alkadienyl with 5 or more carbon atoms (which are unsaturated chain hydrocarbon groups). Specific examples of monocyclic hydrocarbon groups include cycloalkyl with no side chain and with 3 or more carbon atoms and cycloalkyl with a side chain(s) and with 4 or more carbon atoms in total (which are saturated monocyclic hydrocarbon groups); cycloalkenyl with no side chain and with 4 or more carbon atoms, cycloalkynyl with a side chain(s) and with 5 or more carbon atoms in total, cycloalkadienyl with no side chain and with 5 or more carbon atoms and cycloalkadienyl with a side chain(s) and with 6 or more carbon atoms in total (which are unsaturated monocyclic hydrocarbon groups). As aromatic hydrocarbon groups, aromatic groups with no side chain and with 6–14 carbon atoms in total (such as phenyl, 1-naphthyl, 2-naphthyl and 9-anthryl); and aromatic groups with a side chain(s) and with 7 or more carbon atoms in total may be enumerated, for example. Further, phenylphenyl with no side chain and with 12 carbon atoms and phenylphenyl with a side chain(s) and with 13 or more carbon atomsin total (which are also ring-assembling structural hydrocarbon groups) may be enumerated. Specific examples of polycyclic hydrocarbon groups include condensed cyclic hydrocarbon groups with no side chain and with 6 or more carbon atoms; condensed cyclic hydrocarbon groups with a side chain(s) and with 7 or more carbon atoms in total; crosslinked cyclic hydrocarbon groups with no side chain and with 7 or more carbon atoms; crosslinked cyclic hydrocarbon groups with a side chain(s) and with 8 or more carbon atoms in total; spiro hydrocarbon groups with no side chain and with 9 or more carbon atoms; and spiro hydrocarbon groups with a side chain(s) and with 10 or more carbon atoms in total. When one of the condensed rings is a benzene ring in the above-mentioned condensed cyclic hydrocarbon group with no side chain, those hydrocarbon groups with 9 or more carbon atoms in total may be enumerated as specific examples; when one of the condensed rings is a benzene ring in the above-mentioned condensed cyclic hydrocarbon group with a side chain(s), those hydrocarbon groups with 10 or more carbon atoms in total may be enumerated as specific examples. As ring-assembling structural hydrocarbon groups, cycloalkylcycloalkyl with no side chain and with 6 or more carbon atoms in total; cycloalkylcycloalkyl with a side chain(s) and with 7 or more carbon atoms in total; cycloalkylidenecycloalkyl with no side chain and with 6 or more carbon atoms in total; cycloalkylidenecycloalkyl with a side chain(s) and with 7 or more carbon atoms in total; and the like may be enumerated. In these cyclic hydrocarbons, "with a side chain(s)" means that the cyclic hydrocarbon has a chain hydrocarbon(s) on its ring. Specific examples of the chain hydrocarbon groups substituted by the above-described cyclic hydrocarbon group(s) include straight-chain alkyl substituted by an aromatic group that has no side chain and 7 or more carbon atoms in total; straight-chain alkyl substituted by an aromatic group that has a side chain(s) and 8 or more carbon atoms in total; branched-chain alkyl substituted by an aromatic group that has no side chain and 9 or more carbon atoms in total; branched-chain alkyl substituted by an aromatic group that has a side chain(s) and 10 or more carbon atoms in total; straight-chain alkenyl substituted by an aromatic group has no side chain and 8 or more carbon atoms in total; straight-chain alkenyl substituted by an aromatic group that has a side chain(s) and 9 or more carbon atoms in total; branched-chain alkenyl substituted by an aromatic group that has no side chain and 9 or more carbon atoms in total; branched-chain alkenyl substituted by an aromatic group that has a side chain(s) and 10 or more carbon atoms in total; straight-chain alkynyl substituted by an aromatic group that has no side chain and 8 or more carbon atoms in total; straight-chain alkynyl substituted by an aromatic group that has a side chain(s) and 9 or more carbon atoms in total; branched-chain alkynyl substituted by an aromatic group that has no side chain and 10 or more carbon atoms in total; branched chain alkynyl substituted by an aromatic group that has a side chain(s) and 11 or more carbon atoms in total; straight-chain alkadienyl substituted by an aromatic group that has no side chain and 10 or more carbon atoms in total; straight-chain alkadienyl substituted by an aromatic group that has a side chain(s) and 11 or more carbon atoms in total; branched-chain alkadienyl substituted by an aromatic group that has no side chain and 11 or more carbon atoms in total; branched chain alkadienyl substituted by an aromatic group that has a side chain(s) and 12 or more carbon atoms in total; straight-chain alkyl substituted by cycloalkyl that has no side chain and 4 or more carbon atoms in total; straight-chain alkyl substituted by cycloalkyl that has a side chain(s) and 5 or more carbon atoms in total;

branched-chain alkyl substituted by cycloalkyl that has no side chain and 6 or more carbon atoms in total; branched-chain alkyl substituted by cycloalkyl that has a side chain(s) and 7 or more carbon atoms in total; straight-chain alkenyl substituted by cycloalkyl that has no side chain and 5 or more carbon atoms in total; straight-chain alkenyl substituted by cycloalkyl that has a side chain(s) and 6 or more carbon atoms in total; branched-chain alkenyl substituted by cycloalkyl that has no side chain and 6 or more atoms in total; branched-chain alkenyl substituted by cycloalkyl that has a side chain(s) and 7 or more carbon atoms in total; straight-chain alkynyl substituted by cycloalkyl that has no side chain and 5 or more carbon atoms in total; straight-chain alkynyl substituted by cycloalkyl that has a side chain(s) and 6 or more carbon atoms in total; branched-chain alkynyl substituted by cycloalkyl that has no side chain and 7 or more carbon atoms in total; branched-chain alkynyl substituted by cycloalkyl that has a side chain(s) and 8 or more carbon atoms in total; straight-chain alkadienyl substituted by cycloalkyl that has no side chain and 7 or more carbon atoms in total; straight-chain alkadienyl substituted by cycloalkyl that has a side chain(s) and 8 or more carbon atoms in total; branched-chain alkadienyl substituted by cycloalkyl that has no side chain and 8 or more carbon atoms in total; and branched-chain alkadienyl substituted by cycloalkyl that has a side chain(s) and 9 or more carbon atoms in total.

Hereinbelow, aromatic groups with no side chain, aromatic groups with a side chain(s), phenylphenyl with no side chain, phenylphenyl with a side chain(s), and the like will be collectively called "aryl". Also, straight- or branched-chain alkyl substituted by aryl will be called "aralkyl". Similarly, unless otherwise indicated, other cyclic hydrocarbon groups will be called merely "cycloalkyl" or the like when both hydrocarbon groups with no side chain and hydrocarbon groups with a side chain(s) are meant. Chain hydrocarbon groups will also be called merely "alkyl" or the like when both straight-chain and branched-chain hydrocarbon groups are meant.

In the above-mentioned hydrocarbon group, when —$CH_2$— is substituted by carbonyl, sulfonyl, —O— or —S—, ketone, sulfone, ether or thioether structure is introduced, respectively; when —$CH_2$— in —$CH_3$ is substituted by carbonyl, —O— or —S—, the —$CH_3$ is converted to formyl (aldehyde), hydroxyl or mercapto, respectively; when terminal =$CH_2$ is substituted by =O or =S, ketone or thioketone structure is introduced. Further, in the above-mentioned hydrocarbon group, when C—H in —$CH_3$— is changed to N, —NH— is generated; when C—H in >CH— is changed to N, >N— is generated; when C—H in =CH— is changed to N, =N— is generated; when C—H in terminal —$CH_3$ is changed to N, —$NH_2$ is introduced; when C—H in =$CH_2$ is changed to N, =NH is generated; when C—H in C≡CH is substituted by N, the C=CH is converted to C≡N (cyano). When C—H in —$CH_3$, —$CH_2$—, =CH—, ≡CH or >CH— is substituted by C-halogen or C—CN, halogeno or cyano is substituted on the relevant carbon. Substitution with —O—, —S— or N in the carbon chain corresponds to oxa-substitution, thia-substitution or aza-substitution of the relevant hydrocarbon group, respectively. For example, when such substitution occurs in one of the skeleton carbons forming a hydrocarbon ring, the hydrocarbon ring is converted to an oxygen-containing heterocycle, sulfur-containing heterocycle or nitrogen-containing heterocycle. In the above-mentioned hydrocarbon group, substitution in $CH_2$ and substitution in C—H may be performed independently. Besides, if $CH_2$ or C—H still remains on the relevant hydrocarbon group after the above substitution, further substitution may be performed. Furthermore, conversion of —$CH_2$—$CH_2$— to —CO—O— (ester structure) or —CO—S— (thioester structure); conversion of —$CH_2$—$CH_2$—$CH_2$— to —O—CO—O— (carbonic acid ester structure) or —NH—CO—NH— (urea structure) (ureylene); conversion of —$CH_2$—$CH_3$ to —CO—O—H (carboxylic acid structure), —CO—$NH_2$ (amide structure) or —$SO_2$—$NH_2$ (sulfonamide structure), and the like may be performed by the above-mentioned substitution. Halogen means fluorine, chlorine, bromine and iodine, among which fluorine, chlorine and bromine are preferable.

Accordingly, as the $C_{1-14}$ hydrocarbon group represented by $R^2$ or $R^9$ in General Formula (I) described above, either a chain hydrocarbon group or a hydrocarbon group with a cyclic structure (such as cyclic hydrocarbon group) may be selected. Specific examples of the $C_{1-14}$ hydrocarbon group include straight- or branched-chain alkyl (saturated chain hydrocarbon group); straight- or branched-chain alkenyl, straight- or branched-chain alkynyl, straight- or branched-chain alkadienyl and the like (unsaturated chain hydrocarbon groups); cycloalkyl (saturated cyclic hydrocarbon group); cycloalkenyl, cycloalkynyl, cycloalkadienyl and the like (unsaturated cyclic hydrocarbon groups); and aryl, aralkyl, arylalkenyl and the like (aromatic cyclic hydrocarbon groups).

More specifically, as straight- or branched-chain alkyl, methyl, ethyl, propyl, isopropyl, butyl, 1-methylpropyl, pentyl, 1-methylbutyl, hexyl, 1-methylpentyl, heptyl, 1-methylhexyl, 1-ethylpentyl, octyl, nonyl, decyl, undecyl, dodecyl, tridecyl, tetradecyl, 2-methylpropyl, 2-methylbutyl, 3-methylbutyl, 2-methylpentyl, 3-methylpentyl, 4-methylpentyl, methylhexyl, methylheptyl, methyloctyl, methylnonyl, 1,1-dimethylethyl, 1,1-dimethylpropyl, 2,6-dimethylheptyl, 3,7-dimethyloctyl, 2-ethylhexyl or the like may be enumerated. As cycloalkylalkyl, cyclopentylmethyl, cyclohexylmethyl or the like may be enumerated. As cycloalkyl, cyclopropyl, cyclobutyl, cyclopentyl, methylcyclopentyl, cyclohexyl, methylcyclohexyl, cycloheptyl, cyclooctyl or the like may be enumerated. As bicycloalkyl, norbornyl, bicyclo[2.2.2]octyl, adamantyl or the like may be enumerated. As straight- or branched-chain alkenyl, vinyl, allyl, crotyl (2-butenyl), isopropenyl (1-methylvinyl) or the like may be enumerated. As cycloalkenyl or cycloalkadienyl, cyclopentenyl, cyclopentadienyl, cyclohexenyl, cyclohexanedienyl or the like may be enumerated. As straight- or branched-chain alkynyl, ethynyl, propynyl, butynyl, or the like may be enumerated. As aryl, phenyl, 1-naphthyl, 2-naphthyl, 2-phenylphenyl, 3-phenylphenyl, 4-phenylphenyl, 9-anthryl, methylphenyl, dimethylphenyl, trimethylphenyl, ethylphenyl, ethylmethylphenyl, diethylphenyl, propylphenyl, butylphenyl or the like may be enumerated. As aralkyl, benzyl, 1-naphthylmethyl, 2-naphthylmethyl, phenethyl (2-phenylethyl), 1-phenylethyl, phenylpropyl, phenylbutyl, phenylpentyl, phenylhexyl, methylbenzyl, methylphenethyl, dimethylbenzyl, dimethylphenethyl, trimethylbenzyl, ethylbenzyl, diethylbenzyl or the like may be enumerated. As arylalkenyl, styryl, methylstyryl, ethylstyryl, dimethylstyryl, 3-phenyl-2-propenyl or the like may be enumerated.

As the hydrocarbon group represented by $R^2$ or $R^9$ in which $CH_2$ is substituted by carbonyl, sulfonyl, O or S, or in which C—H is substituted by N, C-halogen or C—CN, a group may be given that contains one or more structures such as ketone, aldehyde, carboxylic acid, ester, thioester, amide, carbonic acid ester, carbamic acid ester, sulfone, sulfonamide, ether, thioether, amine, alcohol, thiol, halogen, oxygen-containing heterocycle, sulfur-containing heterocycle or nitrogen-containing heterocycle structure. The oxygen-containing heterocycle, sulfur-containing heterocycle or nitrogen-containing heterocycle means one of the carbons constituting the ring skeleton in a cyclic hydrocarbon group is substituted by oxygen, sulfur or nitrogen, respectively. Further, such a heterocycle may have two or more heteroatom substitutions. Specific examples of hydrocarbon groups having the above-mentioned substitution include acetylmethyl of ketone structure; methanesulfonylmethyl of sulfone structure; methoxymethyl, methoxyethyl, ethoxyethyl, methoxypropyl, butoxyethyl and ethoxyethoxyethyl of ether structure; methylthiomethyl of thioether structure; methylaminomethyl, dimethylaminomethyl, methylaminoethyl, propylaminomethyl and cyclopentylaminomethyl of amine structure; methoxycarbonylmethyl and acetoxymethyl of ester structure; acetylaminomethyl and acetylaminoethyl of amido structure; tetrahydrofuranyl, tetrahydropyranyl and morpholylethyl of oxygen-containing heterocyclic structure; methoxyphenyl of ether structure; methylthiophenyl of thioether structure; acetylphenyl of ketone structure; methoxycarbonyloxyphenyl and ethoxycarbonyloxyphenyl of carbonic acid ester structure; dimethoxyphenyl; methoxycarbonylphenyl, acetoxyphenyl and methylaminocarbonylphenyl of ester structure; furyl of oxygen-containing aromatic ring structure; thienyl of sulfur-containing aromatic ring structure; pyrrolyl, benzofuranyl, imidazolyl, oxazolyl, thiadiazolyl, pyridyl, pyrimidyl, pyridazinyl, pyrazinyl, tetrazinyl, quinolyl, isoquinolyl, pyridylmethyl, phenoxymethyl and benzoyloxymethyl of nitrogen-containing aromatic ring structure; 2-hydroxyethyl of alcohol structure; 2-mercaptoethyl of thiol structure; 2-aminoethyl of amine structure; 2-chloroethyl, 2-hydroxypropyl, 3-hydroxypropyl, 2-mercaptopropyl, 3-mercaptopropyl, 2-aminopropyl, 3-aminopropyl, 2-chloropropyl, 3-chloropropyl, 2,3-dihydroxypropyl, 2,3-dimercaptopropyl, 2,3-diaminopropyl, 2-amino-3-hydroxypropyl, 3-amino-2-hydroxypropyl, 2-hydroxybutyl, 3-hydroxybutyl, 4-hydroxybutyl, 2-aminobutyl, 3-aminobutyl, 4-aminobutyl, 2-mercaptobutyl, 3-mercaptobutyl, 4-mercaptobutyl, 2-chlorobutyl, 3-chlorobutyl, 4-chlorobutyl, 2,3-dihydroxybutyl, 2,4-dihydroxybutyl, 3,4-dihydroxybutyl, 2,3-diaminobutyl, 2,4-diaminobutyl, 3,4-diaminobutyl, 2-amino-3-hydroxybutyl, 3-amino-2-hydroxybutyl, 2-amino-4-hydroxybutyl, 4-amino-2-hydroxybutyl, 3-amino-4-hydroxybutyl, 4-amino-3-hydroxybutyl, 2,3,4-trihydroxybutyl, 2,3,4-triaminobutyl, 2,4-diamino-3-hydroxybutyl, 3-amino-2,4-dihydroxybutyl, 2,3-diamino-4-hydroxybutyl, 4-amino-2,3-dihydroxybutyl, 3,4-diamino-2-hydroxybutyl, 2-amino-3,4-dihydroxybutyl, aminosulfonylphenyl, hydroxyphenyl, aminophenyl, mercaptophenyl, fluorophenyl, chlorophenyl, bromophenyl, cyanophenyl, dihydroxyphenyl, diaminophenyl, difluorophenyl, dichlorophenyl, dibromophenyl, chlorofluorophenyl, trifluorophenyl, trichlorophenyl, fluoromethylphenyl, trifluoromethylphenyl, aminomethylphenyl, hydroxymethylphenyl, hydroxyethylphenyl, aminohydroxyphenyl, fluorohydroxyphenyl, chlorohydroxyphenyl, hydroxycarbonylphenyl and aminocarbonylphenyl.

As preferable examples of $R^2$ in General Formula (I) described above, non-substituted or substituted straight- or branched-chain alkyl, alkenyl or alkadienyl may be enumerated in addition to hydrogen. Specifically, lower alkyl such as methyl, ethyl, propyl, isopropyl, butyl and pentyl; cycloalkyl; cycloalkylalkyl; aryl; and aralkyl, especially non-substituted or substituted benzyl, may be enumerated. Further, C—H in the benzene ring of the above-mentioned benzyl may be substituted by nitrogen. Also, hydrogen on the benzene ring may be substituted by amine. Alternatively, it may be substituted by methyl or the like as a side chain on the ring. In other words, substituted benzyl such as 2-aminobenzyl, 3-aminobenzyl, 4-aminobenzyl; or aza-substituted groups such as 2-pyridylmethyl, 3-pyridylmethyl and 4-pyridylmethyl obtainable by substituting CH of the benzene ring in non-substituted or substituted benzyl by nitrogen are also preferable as $R^2$.

As preferable examples of $R^9$ in General Formula (I) described above, non-substituted or substituted alkyl, in particular, lower alkyl, alkenyl, alkadienyl, cycloalkyl, aryl, aralkyl, in particular, benzyl and substituted benzyl, may be enumerated. Further, C—H in the benzene ring in the above-mentioned benzyl may be substituted by nitrogen; hydrogen on the ring may be substituted by halogeno (particularly, chloro, bromo, fluoro), trifluoromethyl, amino or the like; and lower alkyl such as methyl may be substituted on the ring as a side chain. Besides, alkyl substituted by an aromaticity-exhibiting oxygen-containing heterocycle, sulfur-containing heterocycle or nitrogen-containing heterocycle (which alkyl resembles aralkyl) and the alkyl which further has a substituent(s) or a side chain(s) on the heterocycle are also preferable as $R^9$. Specifically, preferable examples of substituted benzyl include 2-chlorobenzyl, 3-chlorobenzyl, 4-chlorobenzyl, 2-bromobenzyl, 3-bromobenzyl, 4-bromobenzyl, 2-trifluoromethylbenzyl, 3-trifluoromethylbenzyl, 4-trifluoromethylbenzyl, 2-aminobenzyl, 3-aminobenzyl, 4-aminobenzyl, 2, 3-dichlorobenzyl, 3,4-dichlorobenzyl, 3,5-dichlorobenzyl, 4-amino-3-chlorobenzyl, 3-amino-4-chlorobenzyl, 4-amino-3-bromobenzyl, 3-amino-4-bromobenzyl, and aza-substituted groups such as 2-pyridylmethyl, 3-pyridylmethyl and 4-pyridylmethyl obtainable by substituting C—H of the benzene ring in non-substituted or substituted benzyl by nitrogen. Further, in the above-described alkyl substituted by an aromaticity-exhibiting oxygen-containing heterocycle, sulfur-containing heterocycle or nitrogen-containing heterocycle (which alkyl resembles aralkyl) and the alkyl which further has a substituent(s) on the heterocycle, specific examples of the aromaticity-exhibiting oxygen-containing heterocycle, sulfur-containing heterocycle or nitrogen-containing heterocycle constituting such alkyl include furan ring, thiophene ring and pyrrole ring (which are one heteroatom-substituted five-membered rings); oxazole ring, thiazole ring, imidazole ring, isooxazole ring, isothiazole ring and pyrazole ring (which are two heteroatoms-substituted five-membered rings); pyridine ring (which is a mono-aza-substituted benzene ring); pyrimidine ring, pyrazine ring and pyridazine ring (which are di-aza-substituted benzene rings); triazine ring (which is a tri-aza-substituted benzene ring); condensed bicyclic systems formed by condensation of one of these monocycles with the above-mentioned five-membered ring or benzene ring or its aza-substituted six-membered ring (e.g. those formed by condensation of a five-membered ring with a six-membered ring, such as benzofuran, benzothiophene, benzopyrole or benzoimidazole ring; and various azanaphthalene rings, such as quinoline ring, isoquinoline ring and quinoxaline ring, which correspond to aza-substituted forms of naphthalene ring formed by condensation of two six-membered rings); and 4H-pyran-4-one structure or the like which forms with oxo group substituted on the ting a conjugated system resembling an aromatic ring or a structure such as 1,4-dithianaphthalene ring which forms as a whole a conjugated system resembling an aromatic ring. In this alkyl substituted by an aromaticity-exhibiting oxygen-containing heterocycle, sulfur-containing heterocycle or nitrogen-containing heterocycle, a structure resembling non-substituted or substituted benzyl (i.e. methyl group substituted by, in particular, a monocycle of the above-mentioned aromaticity-exhibiting oxygen-containing heterocycle. sulfur-containing heterocycle or nitrogen-containing heterocycle) is regarded as more preferable as non-substituted or substituted benzyl. Further, a preferable substituent(s) or a side chain(s) in substituted benzyl may be substituted on the ring of the above-mentioned structure.

In the amino represented by $R^6$ which is mono- or di-substituted by a $C_{1-10}$ hydrocarbon group(s), the hydrocarbon group means a hydrocarbon group with 10 or less carbon atoms among the various hydrocarbon groups described above. Specific examples of the amino represented by $R^6$ which is mono-substituted by a $C_{1-10}$ hydrocarbon group include methylamino, ethylamino, propylamino, allylamino, butylamino, pentylamino, cyclopropylamino, cyclobutylamino, cyclopentylamino, cyclohexylamino, norbornylamino, bicyclo[2.2.2]octyl amino, phenylamino, naphthylamino, (methylphenyl)amino, (dimethylphenyl)amino, (ethylphenyl)amino, benzylamino, (methylbenzyl) amino, (dimethylbenzyl)amino, (ethylbenzyl)amino and phenetylamino. Specific examples of the amino represented by $R^6$ which is di-substituted by $C_{1-10}$ hydrocarbon groups include dimethylamino, diethylamino, dipropylamino, diallylamino, dibutylamino, methylpropylamino, diphenylamino, bis(methylphenyl) amino, dibenzylamino, bis(methylbenzyl)amino, phenylmethylamino and benzylmethylamino.

The $C_{1-18}$ acyloxy represented by $R^8$ means oxy that has been substituted by acyl resulted from substitution of a $C_{1-17}$ hydrocarbon group selected from the above-described hydrocarbon groups or hydrogen by carbonyl. Specific examples of the $C_{1-18}$ acyloxy include formyloxy, acetyloxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, 2,2-dimethylpropanoyloxy, benzoyloxy, methylbenzoyloxy, dimethylbenzoyloxy, trimethylbenzoyloxy, ethylbenzoyloxy and methoxybenzoyloxy.

The $C_{1-19}$ hydrocarbon group-substituting oxycarbonyloxy represented by $R^8$ means a group in which oxycarbonyloxy is substituted by a $C_{1-19}$ hydrocarbon group selected from the various hydrocarbon groups described above. Specific examples of such oxycarbonyloxy include methoxycarbonyloxy, ethoxycarbonyloxy, propoxycarbonyloxy, butoxycarbonyloxy, pentyloxycarbonyloxy, hexyloxycarbonyloxy, heptyloxycarbonyloxy, octyloxycarbonyloxy, isopropyloxycarbonyloxy, isobutyloxycarbonyloxy, t-butyloxycarbonyloxy, isopentyloxycarbonyloxy and benzyloxycarbonyloxy.

A compound represented by General Formula (I) wherein $R^8$ is acyloxy or hydrocarbon group-substituting oxycarbonyloxy corresponds to an ester of a compound represented by General Formula (I) wherein $R^8$ is hydroxyl; the former compound is a prodrug designed for the purpose of improving the solubility, absorption and stability in the body of the latter compound. When metabolized in the body, the ester is converted into the compound in which $R^8$ is hydroxyl, a real active substance.

A compound represented by General Formula (I) and its tautomer are chemically equivalent, and the purine derivative of the invention includes its tautomer. For example, when $R^8$ is hydroxyl, a compound represented by General Formula (I) is a hydroxy derivative represented by General Formula (II):

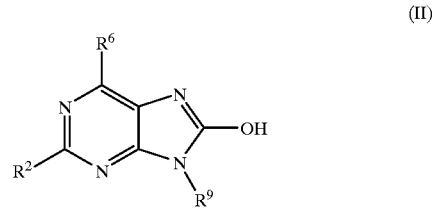

(II)

As a tautomer of the hydroxy derivative, there is an oxo derivative represented by General Formula (III):

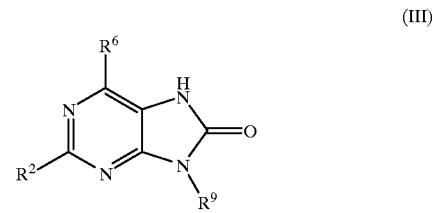

(III)

When $R^6$ is hydroxyl, a compound represented by General Formula (I) is a hydroxy derivative represented by General Formula (IV):

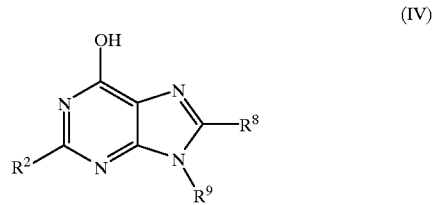

(IV)

As a tautomer of the hydroxy derivative, there is an oxo derivative represented by General Formula (V):

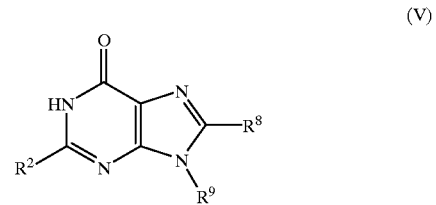

(V)

or General Formula (VI):

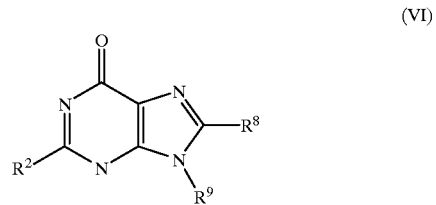

(VI)

As the purine derivative used in the invention, one preferable embodiment is an adenine derivative represented by General Formula (VII), (VIII) or (IX) below wherein $R^6$ is amino or mono- or di-substituted amino:

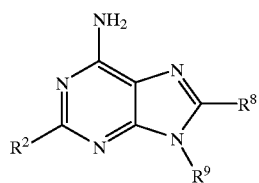

(VII)

wherein $R^2$, $R^8$ and $R^9$ are as defined in General Formula (I);

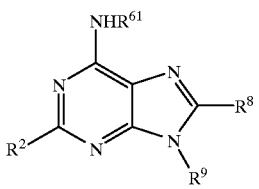

(VIII)

wherein $R^2$, $R^8$ and $R^9$ are as defined in General Formula (I); and $R^{61}$ is a $C_{1-10}$ hydrocarbon group;

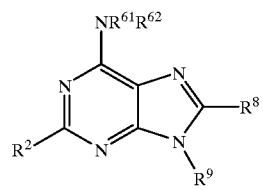

(IX)

wherein $R^2$, $R^8$ and $R^9$ are as defined in General Formula (I); and $R^{61}$ and $R^{62}$ independently represent a $C_{1-10}$ hydrocarbon group.

In particular, the adenine derivative represented by General Formula (VII) is preferable. On the other hand, $R^8$ is preferably hydroxyl or mercapto, more preferably, hydroxyl. Thus, 8-hydroxyadenine derivative represented by General Formula (X):

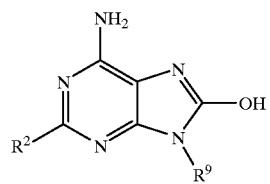

(X)

wherein $R^2$ and $R^9$ are as defined in General Formula (I); is more preferable compound. However, a compound represented by General Formula (VII) wherein $R^8$ is acyloxy or hydrocarbon group-substituting oxycarbonyloxy can be regarded as comparable thereto in one sense since this compound corresponds to a prodrug of the compound represented by General Formula (X).

With respect to $R^2$ and $R^9$, preferable examples are as described above. In $R^9$, selection of non-substituted or substituted benzyl is more preferable. Substituted benzyl as $R^9$ includes such benzyl in which carbon in its benzene ring is substituted by nitrogen. The substituent on the ring includes chain hydrocarbon groups as side chains and groups derived therefrom having various structures such as ketone, aldehyde, carboxylic acid, ester, thioester, amide, carbonic acid ester, carbamic acid ester, sulfone, sulfonamide, ether, thioether, amine, alcohol, thiol or halogen structure derived as a result of substitution of $CH_2$ by carbonyl, sulfonyl, O or S, or substitution of C—H by N, C-halogen or C—CN, as described previously. Among all, halogeno (especially fluoro, chloro and bromo), amino and halogeno-substituting alkyl are more preferable as substituted benzyl.

As $R^2$, non-substituted or substituted alkyl, alkenyl, alkadienyl, cycloalkyl, aryl or aralkyl is more preferable. The substitution in these hydrocarbon groups include such substitution that derives structures such as ketone, aldehyde, carboxylic acid, ester, thioester, amide, carbonic acid ester, carbamic acid ester, sulfone, sulfonamide, ether, thioether, amine, alcohol, thiol or halogen structure as described above; and such substitution in which carbon constituting the ring skeleton of an aromatic ring is replaced by nitrogen. Among all, non-substituted or substituted lower alkyl, non-substituted or substituted benzyl, or non-substituted or substituted cycloalkylalkyl is more preferable.

Hereinbelow, methods of preparation of these purine derivatives will be described in detail.

(1) When $R^8$ is OH or SH a. Outline of Synthesis of 9-Substituted-8-Hydroxyadenine Derivatives or 9-Substituted-8-Mercaptoadenine Derivatives Scheme 1

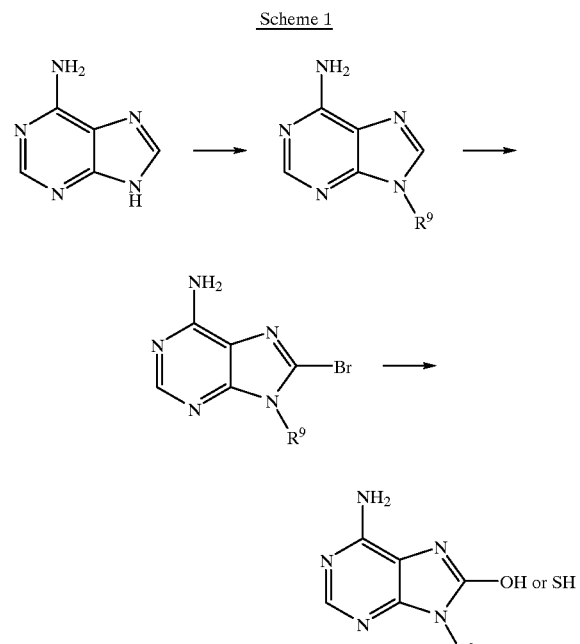

With respect to a compound in which $R^2$ is hydrogen and $R^6$ is $NH_2$, adenine is reacted with various substituted halide containing $R^9$ ($R^9$—X where X is halogen) in the presence of a base such as potassium carbonate, sodium hydroxide or sodium hydride to thereby substitute its position 9 to yield 9-substituted adenine derivative. As a solvent, dimethylformamide, dimethyl sulfoxide, or the like may be used. The solvent may be selected appropriately depending on the base. The reaction temperature may range from room temperature to about 80° C. The resultant 9-substituted adenine derivative is reacted with bromine in the presence of a base such as sodium acetate to yield 9-substituted-8-bromoadenine derivative. As a solvent, acetic acid, chloroform, or the like may be used. The reaction temperature may range from room temperature to about 100° C. Subsequently, when this 9-substituted-8-bromoadenine derivative is reacted with hydrochloric acid, a compound in which $R^8$ is OH, i.e. 9-substituted-8-hydroxyadenine derivative can be prepared. The reaction temperature may range from room temperature to about 100° C. Preferably, the reaction is performed under heating conditions, i.e. at 70–100° C.

On the other hand, when the 9-substituted-8-bromoadenine derivative is reacted with NaSH, a compound in which $R^8$ is SH, i.e. 9-substituted-8-mercaptoadenine derivative can be prepared. As a solvent, alcohol such as methanol or ethanol may be used. The reaction temperature may range from room temperature to a temperature at which the solvent is refluxed. Preferably, the reaction is performed under heating conditions.

b. Outline of Synthesis of 2,9-Disubstituted-8-Hydroxyadenine Derivatives or 2,9-Disubstituted-8-Mercaptoadenine Derivatives tive can be prepared. As a base, sodium ethoxide, sodium methoxide or the like may be used. As a solvent, alcohol such as methanol or ethanol may be used. The reaction temperature may range from room temperature to a temperature at which the solvent is refluxed. Preferably, the reaction is performed under heating conditions.

When this 2,9-disubstituted hypoxanthine derivative is brominated at position 8 and then hydrolyzed or reacted with NaSH in the same manner as described in a. above, a compound which has a substituent at positions 2 and 9 and OH at position 6 can be derived; i.e. 2,9-disubstituted-8-hydroxyhypoxanthine derivative or 2,9-disubstituted-8-mercaptohypoxanthine derivative can be prepared.

On the other hand, the above-mentioned 2,9-disubstituted hypoxanthine derivative is reacted with a chlorinating agent such phosphorus oxychloride or sulfonyl chloride to thereby yield 2,9-disubstituted-6-chloropurine. As a solvent, chloroform or the like may be used. Alternatively, the reaction may be performed without using any solvent. The reaction temperature may range from room temperature to about 100° C. Preferably, the reaction is performed under heating conditions. The resultant 2,9-disubstituted-6-chloropurine is reacted with ammonia or various mono- or di-substituted amine to thereby yield 2,9-disubstituted adenine or 2,9-substituted-6N-substituted adenine. As a solvent, alcohol such as ethanol, dimethylformamide, dimethyl sulfoxide or the like may be used. The reaction temperature may range from room temperature to about 100° C. Preferably, the Scheme 2

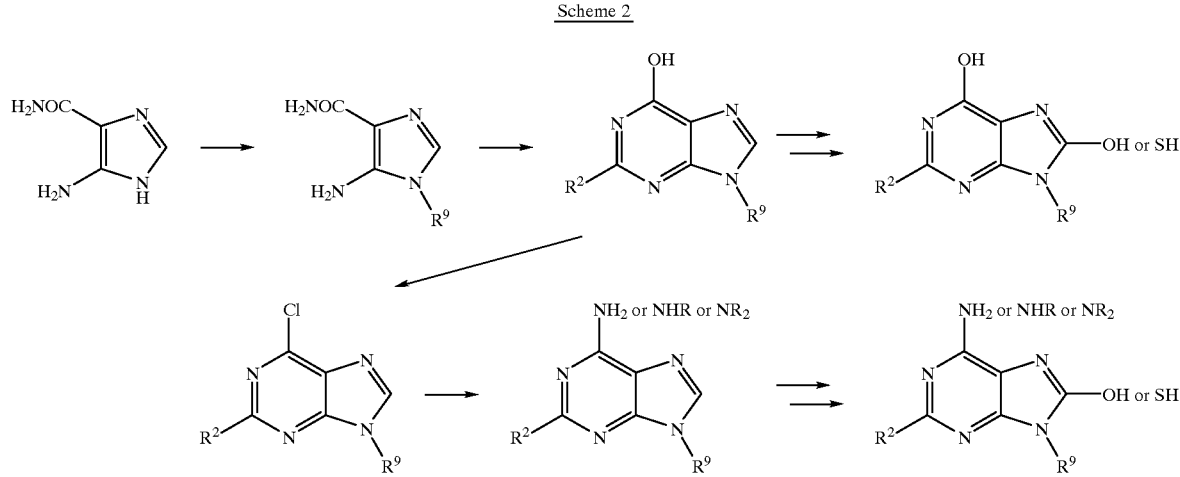

With respect to a compound in which $R^2$ is a substituent, 5-aminoimidazole-4-carboxamide is reacted with various substituted halide containing $R^9$ ($R^9$ —X where X is halogen) in the presence of a base such as sodium hydroxide or sodium hydride to thereby substitute its position 1 to yield 1-substituted-5-aminoimidazole-4-carboxamide. As a solvent, dimethylformamide, dimethyl sulfoxide, or the like may be used. The solvent may be selected appropriately depending on the base. The reaction temperature may range from room temperature to about 80° C. When the resultant 1-substituted-5-aminoimidazole-4-carboxamide is reacted with $R^2$ —COOEt, 2,9-disubstituted hypoxanthine derivareaction is performed under heating conditions. As a base, tertiary amine such as triethylamine may be used if necessary.

When the resultant 2,9-disubstituted adenine or 2,9-substituted-6N-substituted adenine is brominated at position 8 and then hydrolyzed or reacted with NaSH in the same manner as described in a. above, a compound which has a substituent at positions 2 and 9 and amino or substituted amino at position 6 can be derived; i.e. 2,9-substituted-8-hydroxyadenine or 2,9-substituted-8-mercaptoadenine or 2,9-substituted-6N-substituted-8-hydroxyadenine or 2,9-substituted-6N-substituted-8-mercaptoadenine can be derived.

c. Outline of Variation 1 in Synthesis of 2,9-Disubstituted-8-Hydroxyadenine Derivatives or 2,9-Disubstituted-8-Mercaptoadenine Derivatives Scheme 3

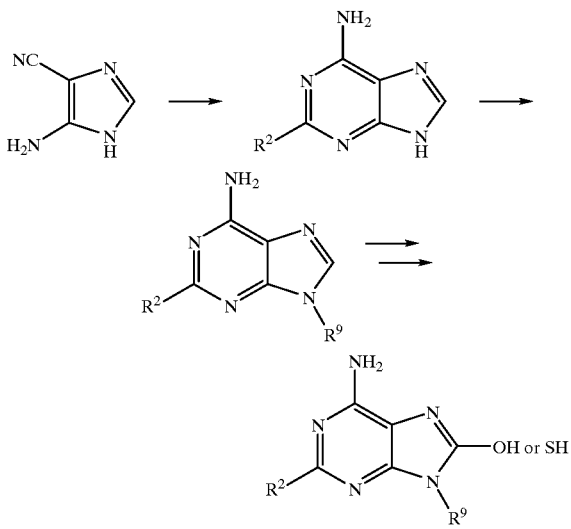

When 5-amino-4-cyanoimidazole is reacted with $R^2CONH_2$, 2-substituted adenine can be derived. No solvent is necessary for this reaction. The two reactants are fused on heating. Preferably, the reaction temperature is high ranging from about 150 to about 240° C. When this 2-substituted adenine is substituted at position 9, brominated and then hydrolyzed or reacted with NaSH in the same manner as described in b. above, a compound which has a substituent at positions 2 and 9 and amino at position 6 can be derived.

d. Outline of Variation 2 in Synthesis of 2,9-Disubstituted-8-Hydroxyadenine Derivatives or 2,9-Disubstituted-8-Mercaptoadenine Derivatives Scheme 4

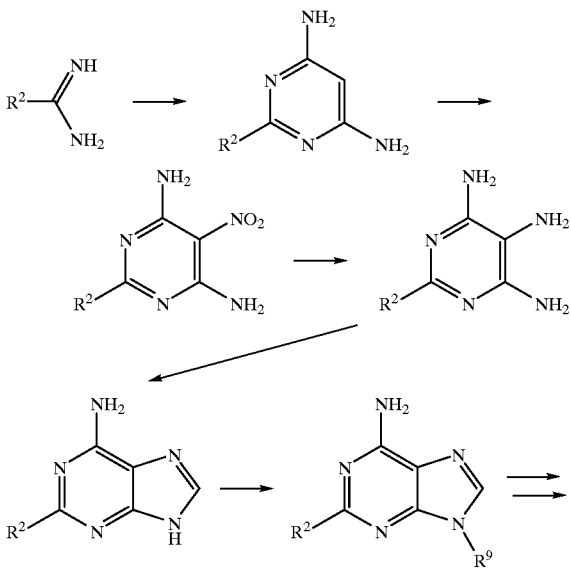

-continued

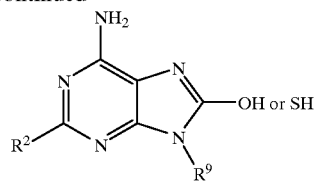

It is also possible to use other method known in the art for forming purine ring. For example, $R^2$-containing amidine (which is the starting material) is reacted with malononitrile to yield a pyrimidine derivative. This derivative is reacted with sodium nitrate or mixed acid to thereby introduce nitro at position 5 of the pyrimidine and then reduced with Pd/C, Pt/C or the like to thereby convert the nitro into amino. It is also possible to react the resultant 2-substituted triaminopyrimidine with orthoester to thereby yield 2-substituted adenine. The subsequent procedures are the same as described in b. above.

(2) When $R^8$ is Acyloxy or Alkoxycarbonyloxy

The purine derivative can be obtained by reacting the compound in which $R^8$ is OH described in (1) above with acyl chloride or chloroformate $R^8$—Cl (which corresponds to a chloride of $R^8$) in the presence of a base such as triethylamine, diisopropylethylamine or dimethylaminopyridine. As a solvent, tetrahydrofuran, 1,4-dioxane, dimethylformamide or the like may be used. The reaction temperature may range from room temperature to about 80° C.

The thus obtained purine derivative (I) may also be used in the form of a pharmaceutical acceptable salt such as sodium salt, potassium salt, hydrochloride, hydrobromide, sulfate, nitrate, acetate, methanesulfonate, toluenesulfonate, citrate, etc.

In the Th2-selective immune response inhibitor and the immune response regulator of the invention, the purine derivative described above effectively treats or prevents those diseases attributable to abnormal rise in immune response on the Th2 side (i.e. allergic diseases such as asthma, allergic dermatitis or allergic rhinitis, or autoimmune diseases such as systemic lupus erythematosus) by inhibiting immune response on the Th2 side and enhancing immune response on the Th1 side. Thus, the immune response inhibitor and the immune response regulator of the invention can be administered for the purpose of treatment or prevention of those diseases. Besides, they are highly safe.

The pharmaceutical composition of the invention may be used in various dosage forms including oral preparations (such as tablets, capsules, powder), injections and external preparations. For example, the purine derivative which is the active ingredient of the pharmaceutical composition of the invention may be mixed with an excipient such as lactose, starch; a lubricant such as magnesium stearate, talc; and other conventional additives and then formulated into tablets. The amount of administration of the pharmaceutical composition of the invention is decided appropriately depending on the sex, age, body weight, disease to be treated, symptoms, etc. of a patient. Generally, the pharmaceutical composition of the invention in the form of an oral preparation is administered in the range from about 0.1 to about 100 mg/kg per day, preferably from about 0.1 to about 20 mg/kg per day, as a single dose or divided dose. In cases such as allergic dermatitis where diseased part is localized on the epidermis, the pharmaceutical composition of the invention may be used in the form of an external preparation such as ointment suitable for percutaneous absorption. In the case of bronchial asthma or allergic rhinitis, the pharmaceutical composition of the invention may also be used in the form of aerosol to be applied to the diseased part directly. The dosage of these local application preparations can be decided appropriately depending on the medium used.

Percutaneous absorbents, specifically ointments, to be applied to allergic dermatitis or the like may be prepared, for example, by the methods described below.

Water-soluble Ointment

A compound represented by General Formula (I) (1.0 g) is placed in a small-size stirring mixer. Pharmacopoeial macrogol ointment (99.0 g) heated to 70° C. is added thereto and mixed for about 30 min under natural cooling. As a result, an ointment containing the compound of General Formula (I) as an active ingredient by 1% can be prepared.

Fat-soluble Ointment

A compound represented by General Formula (I) (1.0 g) is placed in a mortar. Liquid paraffin (18.5 g) is added thereto, and crushed and mixed sufficiently for about 5 min to thereby prepare a suspension. Subsequently, this suspension, white petrolatum (72 g) heated to 70° C. and white beeswax (8.5 g) are placed in a small-size stirring mixer and mixed for about 30 min under natural cooling. As a result, an ointment containing the compound of General Formula (I) as an active ingredient by 1% can be prepared.

The anti-allergic agent of the invention comprising a purine derivative represented by General Formula (I) as an active ingredient is a medicine to be administered for the purpose of ameliorating the symptoms of allergic diseases caused by various factors, or for the purpose of preventing the manifestation of such symptoms. Specifically, the above-mentioned allergic diseases include allergic dermatitis, allergic rhinitis, atopic dermatitis and asthma (both atopic and non-atopic). The anti-allergic agent of the invention is used as a therapeutic or prophylactic for these diseases. Further, the immune response regulator of the invention comprising a purine derivative represented by General Formula (I) as an active ingredient is a drug which regulates helper T cell-involved immune responses into a desirable condition, utilizing the fact that the relevant purine derivative is an inhibitor of immune response on the Th2 side (e.g. IL-4 or IL-5 production) and, at the same time, an enhancer of interferon-γ production by Th1. In the above-mentioned allergic diseases, for example, the immune response regulator of the invention is used in a comprehensive treatment aiming at reduction of patients' burden by not only ameliorating allergic symptoms directly but also inhibiting various viral diseases which are frequently associated with those diseases. In autoimmune diseases such as systemic lupus erythematosus which exhibit similar uncomfortable symptoms, the immune response regulator of the invention may be used in a nosotropic treatment since the regulator selectively inhibits immune response on the Th-2 side. In particular, since it regulates helper T cell-involved immune responses so that a desirable condition will come, amelioration of symptoms as a whole can be achieved.

BEST MODES FOR CARRYING OUT THE INVENTION

Hereinbelow, the purine derivative of the invention used as an active ingredient of the pharmaceutical composition of the invention as well as its pharmacological effects will be described with reference to the following Examples, which should not be construed as limiting the scope of the present invention.

EXAMPLE 1

9-Benzyl-8-Hydroxyadenine 760 mg (2.5 mmol) of 8-bromo-9-benzyladenine was added to concentrated hydrochloric acid and heated for 5 hr under refluxing. The reaction solution was cooled and then neutralized with aqueous ammonia. Deposited crystals were collected by filtration to thereby obtain the captioned compound (534 mg; yield: 88.5%).

$^1$H-NMR (DMSO-$d_6$) δ ppm: 4.91 (2H, s), 6.42 (2H, brs), 7.28 (5H, m), 8.01 (1H, s), 10.22 (1H, brs)

Melting Point: 278–280° C.

Anal.: as $C_{12}H_{10}N_5O$ Calcd. C,59.74; H,4.60; N,29.03; Found C,59.56; H,4.54; N,28.84 (%).

EXAMPLE 2

9-Cyclopentyl-8-Hydroxyadenine

The captioned compound was obtained from 8-bromo-9-cyclopentyladenine by the same procedures as in Example 1 (yield: 64%). The resultant compound was re-crystallized from ethanol.

$^1$H-NMR (DMSO-$d_6$) δ ppm: 1.59 (2H, m), 1.86 (4H, m), 2.11 (2H, m), 4.63 (1H, m), 6.35 (2H, s), 7.99 (1H, s), 10.13 (1H, s)

Melting Point: 229–231° C.

EXAMPLE 3

9-Butyl-8-Hydroxyadenine

The captioned compound was obtained from 8-bromo-9-butyladenine by the same procedures as in Example 1 (yield: 63%). The resultant compound was re-crystallized from ethanol.

$^1$H-NMR (DMSO-$d_6$) δ ppm: 0.96 (3H, t, J=7.3 Hz), 1.35 (2H, m), 1.72 (2H, m), 3.78 (2H, t, J=6.8 Hz), 6.46 (2H, s), 8.09 (1H, s), 10.19 (1H, s)

Melting Point: 222–224° C.

Anal.: as $C_9H_{13}N_5O$ Calcd. C,52.16; H,6.32; N,33.79; Found C,52.01; H,6.26; N,33.59 (%).

EXAMPLE 4

9-(4-Fluorobenzyl)-8-Hydroxyadenine

The captioned compound was obtained from 8-bromo-9-(4-fluorobenzyl)adenine by the same procedures as in Example 1 (yield: 80%). The resultant compound was re-crystallized from ethanol.

$^1$H-NMR (DMSO-$d_6$) δ ppm: 4.97 (2H, s), 6.44 (2H, s), 7.23 (4H, m), 8.01 (1H, s), 10.24 (1H, s)

Melting Point: 270–272° C.

Anal.: as $C_{12}H_{10}N_5OF \cdot 1/5H_2O$ Calcd. C,54.84; H,3.99; N,26.64; Found C,54.97; H,3.87; N,26.38 (%).

EXAMPLE 5

9-(2-Phenylethyl)-8-Hydroxyadenine

The captioned compound was obtained from 8-bromo-9-(2-phenylethyl)adenine by the same procedures as in Example 1 (yield: 81%). The resultant compound was re-crystallized from ethanol.

$^1$H-NMR (DMSO-$d_6$) δ ppm: 3.08 (2H, t), 4.04 (2H, t), 6.47 (2H, s), 7.28 (5H, m), 8.07 (1H, s), 10.19 (1H, s)

Melting Point: 256–258° C.

High Mass: Calcd. 255.1120, Found 255.1116

EXAMPLE 6

9-Benzyl-6-Methylamino-8-Hydroxypurine

The captioned compound was obtained from 8-bromo-9-benzyl-6-methylaminopurine by the same procedures as in Example 1 (yield: 55%).

$^1$H-NMR (DMSO-d$_6$) δ ppm: 3.03 (3H, s), 4.99 (2H, s), 7.30 (5H, m), 8.32 (1H, s), 8.65 (1H, brs), 11.45 (1H, s)

FAB Mass: 256 (M+H)

EXAMPLE 7

9-Benzyl-8-Mercaptoadenine 910 mg (3.0 mmol) of 8-bromo-9-benzyladenine and 1.08 g of sodium hydrosulfide were added to 50 ml of ethanol and heated for 12 hr under refluxing. After the solvent was removed by distillation, the reaction product was dissolved in distilled water and neutralized with 1 N hydrochloric acid. Deposited crystals were collected by filtration to thereby obtain the captioned compound (770 mg; yield: 99%).

TOF-MS: 258 (M+H)

EXAMPLE 8

9-Benzyl-8-Methoxycarbonyloxyadenine 241 mg (1 mmol) of 9-benzyl-8-hydroxyadenine was dissolved in 20 ml of anhydrous THF. To this solution, 202 mg (2 mmol) of triethylamine and 111 mg (0.5 mmol) of dimethylaminopyridine were added and stirred for 1 hr at room temperature. To the resultant mixture, 113 mg (1.2 mmol) of methyl chloroformate was added and stirred overnight at room temperature. 50 ml each of ethyl acetate and water were added thereto for extraction. After the organic layer was removed by vacuum distillation, 20 ml of ether was added to the residue. Then, crystals were collected by filtration (300 mg; yield: 100%).

$^1$H-NMR (CDCl$_3$) δ ppm: 4.06 (3H, s), 5.05 (2H, s), 7.33 (5H, m), 8.25 (1H, s)

Melting Point: 300° C. or above

High Mass: Calcd. 299.1018, Found 299.1006

EXAMPLE 9

9-Benzyl-8-Benzyloxycarbonyloxyadenine

The captioned compound was prepared in the same manner as in Example 8 at a yield of 100% using benzyl chloroformate as an acylating agent for R$^8$.

$^1$H-NMR (CDCl$_3$) δ ppm: 5.04 (2H, s), 5.46 (2H, s), 6.18 (1H, s), 7.41 (10H, m), 8.23 (1H, s)

Melting Point: 300° C. or above

Anal.: as C$_{20}$H$_{10}$N$_5$O$_3$·1/4H$_2$O Calcd. C,63.23; H,4.64; N,18.43; Found C,63.38; H,4.62; N,18.31 (%).

EXAMPLE 10

9-Benzyl-8-tert-Butyloxycarbonyloxyadenine

The captioned compound was prepared in the same manner as in Example 8 at a yield of 100% using di-tert-butyl dicarbonate as an acylating agent for R$^8$.

$^1$H-NMR (CDCl$_3$) δ ppm: 1.73 (9H, s), 5.13 (2H, s), 6.37 (2H, s), 7.45 (5H, m), 8.33 (1H, s)

Melting Point: 287–289° C.

Anal.: as C$_{17}$H$_{19}$N$_5$O$_3$ Calcd. C,59.81; H,5.61; N,20.52; Found C,59.77; H,5.64; N,20.35 (%).

EXAMPLE 11

9-Benzyl-8-Acetoxyadenine

The captioned compound was prepared in the same manner as in Example 8 at a yield of 60% using acetyl chloride as an acylating agent for R$^8$.

Melting Point: 189–191° C.

Anal.: as C$_{14}$H$_{13}$N$_5$O$_2$·1/10H$_2$O Calcd. C,58.98; H,4.67; N,24.57; Found C,59.06; H,4.65; N,24.34 (%).

EXAMPLE 12

9-Benzyl-8-Benzoyloxyadenine

The captioned compound was prepared in the same manner as in Example 8 at a yield of 67% using benzoyl chloride as an acylating agent for R$^8$.

$^1$H-NMR (CDCl$_3$) δ ppm: 5.03 (2H, s), 5.77 (2H, s), 7.28 (3H, m), 7.48 (4H, m), 7.64 (1H, t, J=7.2 Hz), 7.80 (2H, m), 8.35 (1H, s)

Melting Point: 227–229° C.

Anal.: as C$_{19}$H$_{15}$N$_5$O$_2$ Calcd. C,66.08; H,4.38; N,20.28; Found C,65.91; H,4.41; N,20.12 (%).

EXAMPLE 13

9-Benzyl-8-(2,2-Dimethylpropanoyloxy)adenine

The captioned compound was prepared in the same manner as in Example 8 at a yield of 34% using 2,2-dimethylpropanoyl chloride as an acylating agent for R$^8$.

$^1$H-NMR (CDCl$_3$) δ ppm: 1.59 (9H, s), 5.15 (2H, s), 5.60 (2H, s), 7.48 (5H, m), 8.37 (1H, s)

Melting Point: 202–204° C.

EXAMPLE 14

9-Benzyl-8-Pentanoyloxyadenine

The captioned compound was prepared in the same manner as in Example 8 at a yield of 100% using pentanoyl chloride as an acylating agent for R$^8$.

$^1$H-NMR (CDCl$_3$) δ ppm: 0.95 (3H, t, J=7 Hz), 1.42 (2H, m), 1.70 (2H, m), 3.16 (2H, t, J=7 Hz), 5.04 (2H, s), 7.37 (5H, m), 8.24 (1H, s)

Melting Point: 163–165° C.

High Mass: Calcd. 325.1538, Found 325.1525

EXAMPLE 15

9-Benzyl-8-Octanoyloxyadenine

The captioned compound was prepared in the same manner as in Example 8 at a yield of 100% using octanoyl chloride as an acylating agent for R$^8$.

$^1$H-NMR (CDCl$_3$) δ ppm: 0.88 (3H, t), 1.29 (8H, m), 1.72 (2H, m), 3.16 (2H, t), 5.05 (2H, s), 7.38 (5H, m), 8.25 (1H, s)

Melting Point: 248–250° C.

Anal.: as C$_{20}$H$_{25}$N$_5$O$_2$·1/5H$_2$O Calcd. C,64.74; H,6.90; N,18.87; Found C,64.52; H,6.88; N,18.84 (%).

EXAMPLE 16

9-Benzyl-8-Octadecanoyloxyadenine

The captioned compound was prepared in the same manner as in Example 8 at a yield of 71% using octadecanoyl chloride as an acylating agent for R$^8$.

$^1$H-NMR (CDCl$_3$) δ ppm: 0.88 (3H, t), 1.25 (28H, m), 1.70 (2H, m), 3.16 (2H, t), 5.05 (2H, s), 7.40 (5H, m), 8.25 (1H, s)

Melting Point: 128–129° C.

High Mass: Calcd. 507.3573, Found 507.3555

EXAMPLE 17

9-Benzyl-8-Hydroxy-2-Methyladenine 70 mg (0.47 mmol) of 2-methyladenine was dissolved in a mixed solvent composed of DMF (15 ml) and water (5 ml). To this solution, 0.26 g (1.88 mmol) of potassium carbonate and 0.5 ml (about 2 mmol) of benzyl bromide were added and stirred at room temperature for 16 hr. After the solvent was removed by vacuum distillation, the residue was extracted with chloroform, dried over anhydrous magnesium sulfate and then concentrated. The resultant residue was purified by column chromatography (eluent:dichloromethane:methanol=50:1–30:1) to thereby obtain 0.12 g of 9-benzyl-2-methyladenine.

60 mg (0.25 mmol) of this 9-benzyl-2-methyladenine and 0.22 g of sodium acetate were dissolved in 5 ml of acetic acid, to which 0.2 ml of bromine was added. The resultant solution was stirred at 70° C. for 40 min under heating. After the solvent was removed by vacuum distillation, the residue was extracted with ethyl acetate, and the organic layer was vacuum-concentrated. The resultant residue was purified by silica gel column chromatography (eluent:dichloromethane:methanol=50:1) to thereby obtain 60 mg of orange-colored solid. This solid was added to 5 ml of concentrated hydrochloric acid and heated for 3 hr under refluxing. After the reaction solution was cooled, its pH was adjusted to 8 with aqueous ammonia. Then, the deposited solid was vacuum filtered, washed with water and dried to thereby obtain 10 mg of the captioned compound (yield: 16%).

$^1$H-NMR (DMSO-$d_6$) δ ppm: 2.31 (3H, s), 4.89 (2H, s), 6.36 (2H, s), 7.24–7.30 (5H, m), 10.09 (1H, s)

TOF-MS: 256 (M+1)

EXAMPLE 18

9-(m-Chlorobenzyl)-8-Hydroxy-2-Methyladenine

The captioned compound was prepared in the same manner as in Example 17 at a yield of 67% using m-chlorobenzyl chloride.

$^1$H-NMR (DMSO-$d_6$) δ ppm: 2.32 (3H, s), 4.90 (2H, s), 6.38 (2H, s), 7.19–7.35 (4H, m), 10.14 (1H, s)

TOF-MS: 291 (M+1)

EXAMPLE 19

9-Benzyl-8-Mercapto-2-Methyladenine

The captioned compound was prepared in the same manner as in Example 7 at a yield of 8% using 9-benzyl-8-bromo-2-methyladenine.

$^1$H-NMR (DMSO-$d_6$) δ ppm: 2.36 (3H, s), 5.31 (2H, s), 6.79 (2H, s), 7.27–7.31 (5H, m), 12.30 (1H, s)

FAB-MS: 272 (M$^{+1}$)

EXAMPLE 20

9-Benzyl-8-Hydroxy-2-Pentyladenine 1.09 g (11 mmol) of 4-amino-5-cyanoimidazole and 4.39 g (38 mmol) of hexanamide were stirred at 210° C. for 15 hr with heating under an atmosphere of nitrogen. A mixed solvent composed of DMF (200 ml) and water (50 ml) was added thereto. Further, 3.0 ml of benzyl chloride and 3.00 g of potassium carbonate were added thereto. The resultant mixture stirred at 70° C. for 6 hr under heating. After the solvent was removed by vacuum distillation, the residue was taken into water and extracted with dichloromethane. The organic layer was vacuum-concentrated. The residue was purified by silica gel column chromatography (eluent: dichloromethane:methanol=100:1–50:1) to thereby obtain a solid. This solid and 5.00 g of sodium acetate were dissolved in 40 ml of acetic acid. Then, 2 ml of bromine was added to the solution placed in ice bath. Subsequently, the resultant solution was stirred at 70° C. for 6 hours under heating. After the solvent was removed by vacuum distillation, the residue was extracted with ethyl acetate, and the organic layer was vacuum-concentrated. The residue was purified by column chromatography (eluent: dichloromethane:methanol=100:1) to obtain a solid. This solid was added to 20 ml of concentrated hydrochloric acid and heated for 6 hours under refluxing. After the reaction solution was cooled, its pH was adjusted to 8 with aqueous ammonia. The deposited solid was vacuum-filtered, washed with water and then dried to thereby obtain 0.25 g of the captioned compound (yield: 8%).

$^1$H-NMR (DMSO-$d_6$) δ ppm: 0.84 (3H, t, J=6.6 Hz), 1.26 (4H, m), 1.65 (2H, m, J=7.2 Hz), 2.55 (2H, t, J=7.2 Hz), 4.88 (2H, s), 6.34 (2H, s), 7.24–7.29 (5H, m), 10.09 (1H, s)

TOF-MS: 312 (M+1)

EXAMPLE 21

9-Benzyl-2-Cyclohexyl-8-Hydroxyadenine

The captioned compound was prepared in the same manner as in Example 20 at a yield of 13% using cyclohexanecarboxamide.

$^1$H-NMR (DMSO-$d_6$) δ ppm: 1.16–1.85 (11H, m), 4.89 (2H, s), 6.35 (2H, s), 7.23–7.33 (5H, m), 10.14 (1H, s)

TOF-MS: 324 (M+1)

EXAMPLE 22

9-Benzyl-8-Hydroxy-2-Propyladenine

The captioned compound was prepared in the same manner as in Example 20 at a yield of 66% using butanamide.

$^1$H-NMR (DMSO-$d_6$) δ ppm: 0.87 (3H, t, J=7.3 Hz), 1.68 (2H, m, J=7.3 Hz), 2.55 (2H, t, J=7.3 Hz), 4.90 (2H, s), 6.35 (2H, s), 7.21–7.30 (5H, m), 10.11 (1H, s)

TOF-MS 284 (M+1)

EXAMPLE 23

9-Benzyl-8-Hydroxy-2-Phenyladenine

The captioned compound was prepared in the same manner as in Example 20 at a yield of 11% using benzamide.

$^1$H-NMR (DMSO-$d_6$) δ ppm: 5.01 (2H, s), 6.52 (2H, s), 7.23–7.44 (8H, m), 8.37 (2H, dd, J=6.0, 1.9HZ), 10.31 (1H, s)

TOF-MS: 318 (M+1)

EXAMPLE 24

2,9-Dibenzyl-8-Hydroxyadenine

The captioned compound was prepared in the same manner as in Example 20 at a yield of 52% using 2-phenylacetamide.

$^1$H-NMR (DMSO-$d_6$) δ ppm: 3.88 (2H, s), 4.89 (2H, s), 6.40 (2H, s), 7.16–7.28 (10H, m), 10.11 (1H, s)

TOF-MS: 332 (M+1)

EXAMPLE 25

2-(1-Adamantyl)-9-Benzyl-8-Hydroxyadenine

The captioned compound was prepared in the same manner as in Example 20 at a yield of 62% using 1-adamantanecarboxamide.

$^1$H-NMR (DMSO-$d_6$) δ ppm: 1.70 (6H, m), 1.94 (6H, m), 2.02 (3H, m), 4.88 (2H, s), 6.23 (2H, s), 7.24–7.37 (5H, m), 10.11 (1H, s)

TOF-MS: 376 (M+1)

EXAMPLE 26

9-Benzyl-8-Hydroxy-2-(4-Methylphenyl)adenine

The captioned compound was prepared in the same manner as in Example 20 at a yield of 3% using 4-methylbenzamide.

$^1$H-NMR (DMSO-$d_6$) δ ppm: 2.34 (3H, s), 5.00 (2H, s), 6.49 (2H, s), 7.23–7.40 (7H, m), 8.17 (2H, d, J=7.8 Hz), 10.30 (1H, s)

TOF-MS: 332 (M+1)

EXAMPLE 27

9-Benzyl-2-(4-Chlorophenyl)-8-Hydroxyadenine

The captioned compound was prepared in the same manner as in Example 20 at a yield of 8% using 4-chlorobenzamide.

$^1$H-NMR (DMSO-$d_6$) δ ppm: 5.01 (2H, s), 6.59 (2H, s), 7.26–7.40 (5H, m), 7.51 (2H, d, J=8.4 Hz), 8.26 (2H, d, J=8.4 Hz), 10.62 (1H, s)

TOF-MS: 353 (M+1)

EXAMPLE 28

9-Benzyl-8-Hydroxy-2-Isobutyladenine

The captioned compound was prepared in the same manner as in Example 20 at a yield of 34% using 3-methylbutanamide.

$^1$H-NMR (DMSO-$d_6$) δ ppm: 0.86 (6H, d, J=6.8 Hz), 2.11 (1H, m), 2.45 (2H, d), 4.90 (2H, s), 6.35 (2H, S), 7.24–7.31 (5H, m)

TOF-MS: 298 (M+1)

EXAMPLE 29

9-(2,4-Dichlorobenzyl)-8-Hydroxy-2-Methyladenine

The captioned compound was prepared in the same manner as in Example 17 at a yield of 31% using 2,4-dichlorobenzyl chloride.

$^1$H-NMR (DMSO-$d_6$) δ ppm: 2.22 (3H, s), 4.93 (2H, s), 6.42 (2H, s), 6.96 (1H, d, J=8.1 Hz), 7.35 (1H, d, J=8.1 Hz), 6.67 (1H, s), 10.09 (1H, s)

TOF-MS: 325 (M+1)

EXAMPLE 30

9-Benzyl-8-Hydroxy-2-Hydroxymethyladenine

The captioned compound was prepared in the same manner as in Example 20 at a yield of 6% using benzyloxyacetamide.

$^1$H-NMR (DMSO-$d_6$) δ ppm: 4.31 (2H, d, J=6.0 Hz), 4.81 (1H, t, J=6.0 Hz), 6.46 (2H, s), 7.22–7.33 (5H, m), 10.21 (1H, s)

TOF-MS 272 (M+1)

EXAMPLE 31

9-Isobutyl-8-Hydroxy-2-Methyladenine

The captioned compound was prepared in the same manner as in Example 17 at a yield of 20% using isobutyl chloride.

$^1$H-NMR (DMSO-$d_6$) δ ppm: 0.84 (6H, d, J=6.6 Hz), 2.15 (1H, m, J=6.6 Hz), 3.50 (2H, d, J=7.2 Hz), 6.30 (2H, s), 9.99 (1H, s)

TOF-MS: 222 (M+1)

EXAMPLE 32

9-Benzyl-2-tert-Butyl-8-Hydroxyadenine

The captioned compound was prepared in the same manner as in Example 20 at a yield of 3% using 2,2-dimethylpropanamide.

$^1$H-NMR (DMSO-$d_6$) δ ppm: 1.27 (9H, s), 4.88 (2H, s), 6.25 (2H, s), 7.22–7.38 (5H, m), 10.01 (1H, s)

TOF-MS: 298 (M+1)

EXAMPLE 33

9-Benzyl-2-Heptyl-8-Hydroxyadenine

The captioned compound was prepared in the same manner as in Example 20 at a yield of 19% using octanamide.

$^1$H-NMR (DMSO-$d_6$) δ ppm: 0.84 (3H, t, J=7.5 Hz), 1.22–1.24 (8H,m), 1.62–1.67 (2H, m), 2.56 (3H, t, J=7.5 Hz), 4.89 (2H, s,), 6.33 (2H, s), 7.24–7.29 (5H, m), 10.08 (1H, s)

TOF-MS: 340 (M+1)

EXAMPLE 34

9-(2-Chlorobenzyl)-8-Hydroxy-2-Methyladenine

The captioned compound was prepared in the same manner as in Example 17 at a yield of 30% using 2-chlorobenzyl chloride.

$^1$H-NMR (DMSO-$d_6$) δ ppm: 2.28 (3H, s), 4.96 (2H, s), 6.42 (2H, s), 6.89 (1H, d), 7.23–7.32 (2H, m), 7.50 (1H, d), 10.20 (1H, s)

TOF-MS: 291 (M+1)

EXAMPLE 35

9-(4-Chlorobenzyl)-8-Hydroxy-2-Methyladenine

The captioned compound was prepared in the same manner as in Example 17 at a yield of 42% using 4-chlorobenzyl chloride.

$^1$H-NMR (DMSO-$d_6$) δ ppm: 2.31 (3H, s), 4.89 (2H, s), 6.37 (2H,s), 7.28 (2H, d), 7.38 (2H, d), 10.11 (1H, s)

TOF-MS: 291 (M+1)

EXAMPLE 36

9-(3-Bromobenzyl)-8-Hydroxy-2-Methyladenine

The captioned compound was prepared in the same manner as in Example 17 at a yield of 59% using 3-bromobenzyl chloride.

$^1$H-NMR (DMSO-$d_6$) δ ppm: 2.33 (3H, s), 4.90 (2H, s), 6.35 (2H, s), 7.14–7.38 (4H, m), 10.16 (1H, s)

TOF-MS: 335 (M+1)

EXAMPLE 37

8-Hydroxy-2-Methyl-9-(4-Methylbenzyl)adenine

The captioned compound was prepared in the same manner as in Example 17 at a yield of 62% using 4-methylbenzyl chloride.

$^1$H-NMR (DMSO-d$_6$) δ ppm: 2.26 (3H, s), 2.33 (3H, s), 4.90 (2H, s), 6.38 (2H, s), 7.14 (2H, d), 7.22 (2H, d), 10.14 (1H, s)

TOF-MS: 270 (M+1)

EXAMPLE 38

8-Hydroxy-9-(4-Methoxybenzyl)-2-Methyladenine

The captioned compound was prepared in the same manner as in Example 17 at a yield of 52% using 4-methoxybenzyl chloride.

$^1$H-NMR (DMSO-d$_6$) δ ppm: 2.26 (3H, s), 3.72 (3H, s), 4.88 (2H, s), 6.39 (2H, s), 6.90 (2H, d), 7.31 (2H, d), 10.14 (1H, s)

TOF-MS: 286 (M+1)

EXAMPLE 39

9-(4-tert-Butylbenzyl)-8-Hydroxy-2-Methyladenine

The captioned compound was prepared in the same manner as in Example 17 at a yield of 57% using 4-tert-butylbenzyl chloride.

$^1$H-NMR (DMSO-d$_6$) δ ppm: 1.23 (9H, s), 2.28 (3H, s), 4.89 (2H, s), 6.40 (2H, s), 7.25 (2H, d), 7.36 (2H, d), 10.15 (1H, s)

TOF-MS: 312 (M+1)

EXAMPLE 40

8-Hydroxy-2-Methyl-9-(α-Methylbenzyl)adenine

The captioned compound was prepared in the same manner as in Example 17 at a yield of 69% using α-methylbenzyl chloride.

$^1$H-NMR (DMSO-d$_6$) δ ppm: 1.95 (3H, d), 2.28 (3H, s), 4.89 (2H, s), 5.81 (1H, m), 6.39 (2H, s), 7.25–7.36 (5H, m), 10.13 (1H, s)

TOF-MS: 270 (M+1)

EXAMPLE 41

8-Hydroxy-2-Methyl-9-(1-Naphthylmethyl)adenine

The captioned compound was prepared in the same manner as in Example 17 at a-yield of 52% using 1-naphthylmethyl chloride.

$^1$H-NMR (DMSO-d$_6$) δ ppm: 2.28 (3H, s), 5.42 (2H, s), 6.39 (2H, s), 7.20–8.01 (7H, m), 10.15 (1H, s)

TOF-MS: 306 (M+1)

EXAMPLE 42

8-Hydroxy-2-Methyl-9-(2-Naphthylmethyl)adenine

The captioned compound was prepared in the same manner as in Example 17 at a yield of 67% using 2-naphthylmethyl chloride.

$^1$H-NMR (DMSO-d$_6$) δ ppm: 2.29 (3H, s), 5.22 (2H, s), 6.39 (2H, s), 7.49–7.88 (7H, m), 10.12 (1H, s)

TOF-MS 306 (M+1)

EXAMPLE 43

8-Hydroxy-2-Methyl-9-(3-Trifluoromethylbenzyl)adenine

The captioned compound was prepared in the same manner as in Example 17 at a yield of 72% using 3-trifluoromethylbenzyl chloride.

$^1$H-NMR (DMSO-d$_6$) δ ppm: 2.28 (3H, s), 5.12 (2H, s), 6.38 (2H, s), 7.57–7.76 (4H, m), 10.15 (1H, s)

TOF-MS: 324 (M+1)

EXAMPLE 44

9-(2,3-Dichlorobenzyl)-8-Hydroxy-2-Methyladenine

The captioned compound was prepared in the same manner as in Example 17 at a yield of 60% using 2,3-dichlorobenzyl chloride.

$^1$H-NMR (DMSO-d$_6$) δ ppm: 2.28 (3H, s), 5.15 (2H, s), 6.39 (2H, s), 6.99 (1H, m), 7.32 (1H, m), 7.61 (1H, m), 10.13 (1H, s)

TOF-MS: 325 (M+1)

EXAMPLE 45

9-Benzyl-8-Hydroxy-2-Isopropyladenine

The captioned compound was prepared in the same manner as in Example 20 at a yield of 14% using 2-methyilpropanamide.

$^1$H-NMR (DMSO-d$_6$) δ ppm: 1.51 (6H, d), 2.15 (2H, s), 4.89 (2H, s), 6.39 (2H, d), 7.41 (5H, d), 10.13 (1H, s),

TOF-MS: 284 (M+1)

EXAMPLE 46

8-Hydroxy-2-Methyl-9-(3-Pyridylmethyl)adenine

The captioned compound was prepared in the same manner as in Example 17 at a yield of 25% using 3-pyridylmethyl chloride.

$^1$H-NMR (DMSO-d$_6$) δ ppm: 2.35 (3H, s), 4.93 (2H, m), 6.42 (2H, s), 7.17 (1H, d), 7.27–7.32 (1H, m), 7.29–7.79 (1H, m), 8.48 (1H, d), 10.15 (1H, s)

TOP-MS: 256 (M+1)

EXAMPLE 47

8-Hydroxy-2-Methyl-9-(2-Pyridylmethyl)adenine

The captioned compound was prepared in the same manner as in Example 17 at a yield of 24% using 2-pyridylmethyl chloride.

$^1$H-NMR (DMSO-d$_6$) δ ppm: 2.31 (3H, s), 4.95 (2H, s), 6.42 (2H, s), 7.20 (1H, d), 7.28 (7H, dd), 7.79 (1H, md), 8.48 (1H, d), 10.10 (1H, s)

TOF-MS 256 (M+1)

EXAMPLE 48

8-Hydroxy-2-Methyl-9-(4-Pyridylmethyl)adenine

The captioned compound was prepared in the same manner as in Example 17 at a yield of 31% using 4-pyridylmethyl chloride.

$^1$H-NMR (DMSO-d$_6$) δ ppm: 2.30 (3H,s), 4.98 (2H, s), 6.42 (2H, s), 7.20 (2H, d), 8.54 (2H, d), 10.18 (1H, s)

TOF-MS: 256. (M+1)

EXAMPLE 49

9-Benzyl-8-Hydroxy-2-( 3-Pyridyl)adenine

The captioned compound was prepared in the same manner as in Example 20 at a yield of 11% using nicotinamide.

$^1$H-NMR (DMSO-$d_6$) δ ppm: 4.87 (2H, s), 6.40 (2H, 1), 7.27–7.36 (5H), m), 7.57 (2H, s d), 8.40 (1H, d), 8.71 (1H, d), 9.1 9 (1H, s), 10.17 (1H, s)

TOF-MS 318 (M+1)

EXAMPLE 50

9-Benzyl-8-Hydroxy-2-5(-Naphthylmethyl)adenine

The captioned compound was prepared in the same manner as in Example 20 at a yield of 22% using 2-(naphthalene-1-yl)acetamide.

$^1$H-NMR (DMSO-$d_6$) δ ppm: 3.89 (2H, s), 5.42 (2H, s), 6.39 (2H, s), 7.18–8.05 (12H, m), 10.15 (1H, s)

TOF-MS 382 (M+1)

EXAMPLE 51

9-Benzyl-8-Hydroxy-2-(2-Naphthylmethyl)adenine

The captioned compound was prepared in the same manner as in Example 20 at a yield of 34% using 2-(naphthalene-2-yl)acetamide.

$^1$H-NMR (DMSO-$d_6$) δ ppm: 3.95 (2H, s), 5.20 (2H, s), 6.41 (2H, s), 7.49–7.90 (12H, m), 10.14 (1H, s)

TOF-MS: 382 (M+1)

EXAMPLE 52

9-Benzyl-2-Cyclopropyl-8-Hydroxyadenine

The captioned compound was prepared in the same manner as in Example 20 at a yield of 9% using cyclopropanecarboxamide.

$^1$H-NMR (DMSO-$d_6$) δ ppm: 0.84–0.96 (4(H, m), 1.94–1.99(1H, m), 4.88 (211, s), 6.40 (2H, s), 7.38 (5H, m), 10.16 (1H, s)

TOF-MS: 282 (M+1)

EXAMPLE 53

9-Benzyl-8-Hydroxy-2 (2-Pyridylmethyl)adenine

The captioned compound was prepared in the same manner as in Example 20 at a yield of 16% using 2-(pyridine-2-yl)acetamide.

$^1$H-NMR (DMSO-$d_6$) δ ppm: 3.75 (2H, s), 4.87 (2H, s), 6.42 (2H, s), 7.24 (5H, d), 7.28–7.59 (6H, m), 7.79 (1H, dd), 8.51 (1H, d), 10.10 (1H, s)

TOF-MS: 333 (M+1)

EXAMPLE 54

9-Benzyl-8-Hydroxy-2-(3-Pyridylmethyl)adenine

The captioned compound was prepared in the same manner as in Example 20 at a yield of 21% using 2-(pyridine-3-yl)acetamide.

$^1$H-NMR (DMSO-$d_6$) δ ppm: 3.88 (2H, s), 4.87 (2H, s), 6.42 (2H, s), 7.20–7.55 (8H, m), 8.52 (1H, d), 10.09 (1H, s)

TOF-MS 333 (M+1)

EXAMPLE 55

9-Benzyl-8-Hydroxy-2-(4-Pyridylmethyl)adenine

The captioned compound was prepared in the same manner as in Example 20 at a yield of 32% using 2-(pyridine-4-yl)acetamide.

$^1$H-NMR (DMSO-$d_6$) δ ppm: 3.92 (2H, s), 4.87 (2H, s), 6.41 (2H, s), 7.19–7.54 (7H, m), 8.52 (2H, d), 10.10 (1H, s)

TOF-MS:.333 (M+1)

EXAMPLE 56

9-4-Aminobenzyl )-8-Hydroxy-2-Methyladenine 9-(4-Nitrobenzyl)-2-methyl-8-hydroxyadenine was prepared in the same manner as in Example 17 at a yield of 36% using 4-nitrobenzyl chloride. 300 mg of the resultant compound and 30 mg of 5% Pd/C were added to 30 ml of ethanol, and stirred at room temperature for 24 hr under an atmosphere of hydrogen. Insoluble matters were removed by filtration. The filtrate was subjected to vacuum distillation to thereby obtain the captioned compound at a yield of 74%.

$^1$H-NMR (DMSO-$d_6$) δ ppm: 2.30 (3H1, s), 4.99 (2H, s), 6.41 (2H, s), 6.83 (2H, s), 7.30 (2H, d), 7.40 (2H, d), 10.14 (1H, s)

TOF-MS: 271 (M+1)

EXAMPLE 57

Inhibitory Effect on Th2-Type Cytokine Production from Sensitized Spleen Cells

1) Preparation of Sensitized Mouse Spleen Cells

Seven week-old male BALB/c mice were immunized with 4 mg of aluminium hydroxide gel (100 μl) adsorbing 10 μg of ovalbumin (OVA) by intraperitoneal administration. After 14 days, the mice received a booster injection of the same composition. Seven days after the booster administration, the spleen was removed and suspended in RPMI-1640 medium containing inactivated bovine fetal serum (10% v/v), 2-mercaptoethanol (50 μM), penicillin G (100 U/ml) and streptomycin (100 μg/ml) to prepare a cell suspension.

2) Cytokine Production Induced by Antigen Stimulation

To the spleen cell suspension (5×10$^6$ cells/200 μl/well), 1/1000 volume of dimethyl sulfoxide solution dissolving OVA (0.5 mg/ml) and a test compound at a specific concentration was added. Then, the cells were cultured at 37° C. under 5% $CO_2$. After 3 days, cytokines in the culture supernatant were determined by ELISA. Specifically, as a Th1 type cytokine, interferon-γ, (IFN-γ) was determined using Mouse IFN-γ ELISA Kit (Amersham). As Th2 type cytokines, interleukin-4 (IL-4) and interleukin-5 (IL-5) were determined with Mouse IL-4 ELISA Kit (Amersham) and Mouse IL-5 ELISA minikit (Endogen), respectively.

Whether or not the test compound exhibited cytotoxicity was judged based on the ability of the above-mentioned splenic cells cultured for three days to biologically reduce 3-(4,5-dimethylthiazole-2-yl)-5-(3-carboxymethoxyphenyl)-2-(4-sulfophenyl)-2H-tetrazolium salts (MTS). The cells' ability to biologically reduce MTS was determined with Cell Titer 96 AQueous Kit (Promega). The results are shown in Table 1.

TABLE 1

| Group | Concentration (μM) | IL-4 (pg/ml) | IL-5 (pg/ml) | IFN-γ (ng/ml) |
|---|---|---|---|---|
| OVA (−) | — | <7.8 | 79 | 14 |
| OVA (+) | — | 282 | 4,143 | 25 |

TABLE 1-continued

| Group | Concentration ($\mu$M) | IL-4 (pg/ml) | IL-5 (pg/ml) | IFN-$\gamma$ (ng/ml) |
|---|---|---|---|---|
| Example 18 | 0.1 | 254 | 4,150 | 26 |
|  | 1 | <7.8 | 2,321 | 63 |
|  | 10 | <7.8 | 710 | 181 |
| Example 19 | 0.1 | 296 | 4,482 | 16 |
|  | 1 | 29 | 1,782 | 50 |
|  | 10 | <7.8 | 643 | 139 |
| Example 20 | 0.01 | 208 | 3,792 | 25 |
|  | 0.1 | 20 | 1,667 | 135 |
|  | 1 | <7.8 | 670 | 193 |
|  | 10 | <7.8 | 524 | 219 |
| Example 21 | 0.1 | 192 | 4,103 | 28 |
|  | 1 | 11 | 1,291 | 158 |
|  | 10 | <7.8 | 715 | 170 |
| Example 24 | 0.1 | 195 | 3,670 | 44 |
|  | 1 | <7.8 | 1,130 | 199 |
|  | 10 | <7.8 | 345 | 244 |
| Example 45 | 0.1 | 86 | 2,881 | 46 |
|  | 1 | <7.8 | 699 | 161 |
|  | 10 | <7.8 | 563 | 187 |

As shown in Table 1, the purine derivative used in the present invention inhibits cytokine production on the Th2 side and, at the same time, enhances cytokine production on the Th1 side in a dose dependant manner. Further, any of the test compounds did not exhibit concentration range shown in Table 1.

EXAMPLE 58

Inhibitory Effect on Eosinophilic Infiltration

Eight week-old male BALB/c mice were immunized with 1.6 mg of aluminium hydroxide gel (200 $\mu$l) adsorbing 100 $\mu$g of OVA by subcutaneous administration in the back. After 7 days, the mice received a booster injection of the same composition. Seven days after the booster administration, 10 $\mu$g of OVA in 200 $\mu$l of physiological saline was administered to the mice intraperitoneally. Two days after the intraperitoneal administration, abdominal cavity-infiltrating cells were collected with physiological saline. The total cell count and the eosinophile count in the collected cells were calculated by staining with Türk's solution and Hinkerman's solution, respectively. The test compound was administered orally 2 hours before the OVA intraperitoneal administration.

TABLE 2

| Compound | Dose (mg/kg) | Ratio of Infiltrating Eosinophiles (%) | Inhibition (%) |
|---|---|---|---|
| Control | — | 12.66 | — |
| Example 17 | 30 | 4.70 | 62.9 |
| Example 20 | 30 | 6.94 | 46.2 |
| Dexamethasone | 3 | 10.27 | 18.9 |

As shown in Table 2, the purine derivative represented by General Formula (I) which is the active ingredient of the pharmaceutical composition of the invention has an activity of reducing the ratio of eosinophiles infiltrating into the abdominal cavity.

EXAMPLE 59

2-Butyl-9-(p-Fluorobenzyl)-8-Hydroxyadenine

The captioned compound was prepared based on the method as described in Example 20.

$^1$H-NMR (DMSO-d$_6$) $\delta$ ppm: 0.87 (3H, t, J=7.6 Hz), 1.28 (2H, tq, J=7.3 Hz, J=7.3 Hz), 1.64 (2H, tt, J=7.6 Hz, J=7.3 Hz), 2.56 (2H, t, J=7.6 Hz), 4.89 (2H, s), 6.37 (2H, s), 7.11–7.38 (4H, m), 10.15 (1H, s)

EXAMPLE 60

Anti-allergic Effect

It was proved that the compound of Example 59 can be used as a therapeutic for or an inhibitor of allergic diseases, particularly, allergic dermatitis because this compound has the above-described selective inhibitory effect on immune response on the Th2 side. It was demonstrated that the pharmaceutical composition of the invention reveals therapeutic effect as an ointment applied to the affected part directly, using mouse FITC (fluoresceine isothiocyanate)-induced contact dermatitis model as an allergic dermatitis model. As a control, Imiquimode (R-837; 4-amino-1-isobutyl-1H-imidazo[4,5-c]quinoline) disclosed in EP 145, 340 A was used for comparison. Further, a steroid-type drug Rinderon™ ointment (Shionogi & Co.; 0.12% betamethasone valerate ointment) was used for reference.

Preparation of Macrogol Ointments

The test compound was dissolved in an ointment base (PEG400:PEG4000=7:3) heated to about 80° C. to give a concentration of 1 mg/ml or 10 mg/ml, and then cooled to solid at room temperature to thereby prepare 0.1 or 1% macrogol ointment. Imiquimode (R-837), the control, was also formulated into 0.1 and 1% macrogol ointments.

Test Method

Seven week-old male BALB/c mice were sensitized by applying 0.2 ml of 0.5% FITC in acetone/dibutyl phthalate (1:1) to the abdomen sheared in advance. Seven days after the sensitization, inflammation was induced by applying 10 $\mu$l of 0.5% FITC in acetone/dibutyl phthalate (1:1) to each side of the left auricule (total 20 $\mu$l). Before the induction and 24 hr after the induction, the thickness of the auricule was measured with a micrometer. The difference between the two values was taken as the swelling degree. The macrogoal ointment containing the test compound and Rinderon™ ointment (0.12% betamethasonevalerate) were applied to each side of the left auricule in an amount of 5 $\mu$l (total 10 $\mu$l) 2 hr before the induction. Mice in the placebo group were treated with the macrogol ointment base (PEG400:PEG4000=7:3).

Evaluation Results

The inflammation inhibitory effect of the ointment of the invention was calculated as an inhibition ratio relative to the swelling degree in the placebo group which was taken as 100%. For example, the inhibition ratios in the groups treated with ointments containing 0.1% and 1% of the compound of Example 59, i.e. 2-butyl-9-(p-fluorobenzyl)-8-hydroxyadenine were 67% and 33%, respectively. Although the inhibitory effect exhibited a bell-shaped dose-dependency, it was confirmed that this compound shows a high inhibitory effect at low doses.

With respect to the control compound R-837, the inhibition ratios in the groups treated with 0.1% and 1% ointments were 50% and 67%, respectively. The inhibition ratio in the group treated with Rinderon™ ointment was 94%.

From the above results, it was confirmed that the composition of the invention is absorbed percutaneously and that the composition exhibits pharmacological effect on allergic dermatitis when administered as an external ointment. In view of its high inflammation inhibitory effect at low doses, the pharmaceutical composition of the invention is judged to be suitable as an ointment which is applied repeatedly and should have persistent therapeutic effect.

Industrial Applicability

The pharmaceutical composition of the invention selectively inhibits those immune responses resulted from abnormal exasperation of type 2 helper T cells. Since the pharmaceutical composition of the invention inhibits cytokine production on the Th2 side and, at the same time, enhances cytokine production on the Th1 side, it is useful as a therapeutic for those diseases caused by abnormal exasperation of Th2, e.g. asthma and atopic dermatitis.

What is claimed is:

1. A method of inhibiting a type 2 helper T cell-selective immune response in a subject in need thereof, comprising administering to the subject a composition comprising a purine derivative represented by General Formula (I)

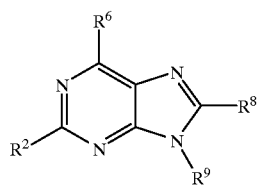

(I)

wherein $R^2$ is hydrogen or a $C_{1-14}$ hydrocarbon in which —$CH_2$— not directly bound to the purine skeleton and $CH_2$ in —$CH_3$ not directly bound to the purine skeleton may be substituted by carbonyl, sulfonyl, —O— or —S—; =$CH_2$ may be substituted by =O or =S; C—H in $CH_2$— not directly bound to the purine skeleton, C—H in —$CH_3$ not directly bound to the purine skeleton, C—H in >CH— not directly bound to the purine skeleton, C—H in =CH— not directly bound to the purine skelton and C—H in =$CH_2$ may be substituted by N, C-halogen or C—CN;

$R^6$ is hydroxyl, amino or amino which is mono- or di-substituted by a $C_{1-10}$ hydrocarbon group(s);

$R^8$ is hydroxyl, mercapto, $C_{1-18}$ acyloxy or $C_{1-19}$ hydrocarbon group-substituting oxycarbonyloxy; and $R^9$ is a $C_{1-14}$ hydrocarbon group in which —$CH_2$— not directly bound to the purine skeleton and $CH_2$ in —$CH_3$ not directly bound to the purine skeleton may be substituted by carbonyl, sulfonyl, —O— or —S—; =$CH_2$ may be substituted by =O or =S; C—H in —$CH_2$— not directly bound to the purine skeleton, C—H in —$CH_3$ not directly bound to the purine skeleton, C—H in >CH— not directly bound to the purine skeleton, C—H in =CH— not directly bound to the purine skeleton, C—H in =$CH_2$ and C—H in ≡CH may be substituted by N, C-halogen or C—CN;

or its tautomer or a pharmaceutically acceptable salt of the purine derivative or the tautomer to inhibit a type 2-helper T cell-selective immune response.

2. A method of inhibiting a type 2 helper T cell-selective immune response in a subject in need thereof, comprising:

providing a composition comprising a purine derivative represented by General Formula (I)

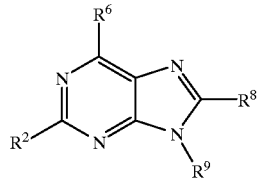

(I)

wherein $R^2$ is hydrogen or a $C_{1-14}$ hydrocarbon in which —$CH_2$— not directly bound to the purine skeleton and $CH_2$ in —$CH_3$ not directly bound to the purine skeleton may be substituted by carbonyl, sulfonyl, —O— or —S—; =$CH_2$ may be substituted by =O or =S; C—H in —$CH_2$— not directly bound to the purine skeleton, C—H in —$CH_3$ not directly bound to the purine skeleton, C—H in >CH— not directly bound to the purine skeleton, C—H in =CH— not directly bound to the purine skelton and C—H in =$CH_2$ may be substituted by N, C-halogen or C—CN;

$R^6$ is hydroxyl, amino or amino which is mono- or di-substituted by a $C_{1-10}$ hydrocarbon group(s);

$R^8$ is hydroxyl, mercapto, $C_{1-18}$ acyloxy or $C_{1-19}$ hydrocarbon group-substituting oxycarbonyloxy; and $R^9$ is a $C_{1-14}$ hydrocarbon group in which —$CH_2$— not directly bound to the purine skeleton and $CH_2$ in —$CH_3$ not directly bound to the purine skeleton may be substituted by carbonyl, sulfonyl, —O— or —S—; =$CH_2$ may be substituted by =O or =S; C—H in —$CH_2$— not directly bound to the purine skeleton, C—H in —$CH_3$ not directly bound to the purine skeleton, C—H in >CH— not directly bound to the purine skeleton, C—H in =CH— not directly bound to the purine skeleton, C—H in =$CH_2$ and C—H in ≡CH may be substituted by N, C-halogen or C—CN;

or its tautomer or a pharmaceutically acceptable salt of the purine derivative or the tautomer; and contacting the composition, directly or indirectly, to a type 2 helper T cell to inhibit a type 2 helper T cell-selective immune response.

3. The method of claim 1, wherein the composition is used as an anti-allergic agent.

4. The method of claim 1, wherein the composition is used as an immune response regulator.

5. A method of treating or preventing an allergic disease in a subject in need thereof, comprising administering to the subject a composition comprising a purine derivative represented by General Formula (I)

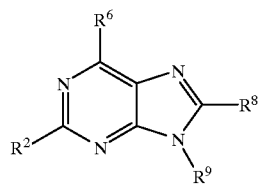

(I)

wherein $R^2$ is hydrogen or a $C_{1-14}$ hydrocarbon in which —$CH_2$— not directly bound to the purine skeleton and $CH_2$ in —$CH_3$ not directly bound to the purine skeleton may be substituted by carbonyl, sulfonyl, —O— or —S—; =$CH_2$ may be substituted by =O or =S; C—H in —$CH_2$— not directly bound to the purine skeleton, C—H in —$CH_3$ not directly bound to the purine skeleton, C—H in >CH— not directly bound to the purine skeleton, C—H in =CH— not directly bound to the purine skelton and C—H in =$CH_2$ may be substituted by N, C-halogen or C—CN;

$R^6$ is hydroxyl, amino or amino which is mono- or di-substituted by a $C_{1-10}$ hydrocarbon group(s);

$R^8$ is hydroxyl, mercapto, $C_{1-18}$ acyloxy or $C_{1-19}$ hydrocarbon group-substituting oxycarbonyloxy; and $R^9$ is a $C_{1-14}$ hydrocarbon group in which —$CH_2$— not directly bound to the purine skeleton and $CH_2$ in —$CH_3$ not directly bound to the purine skeleton may be substituted by carbonyl, sulfonyl, —O— or —S—; =$CH_2$ may be substituted by =O or =S; C—H in —CH$_2$— not directly bound to the purine skeleton, C—H in —CH$_3$ not directly bound to the purine skeleton, C—H in >CH— not directly bound to the purine skeleton, C—H in =CH— not directly bound to the purine skeleton, C—H in =CH$_2$ and C—H in ≡CH may be substituted by N, C-halogen or C—CN; or its tautomer or a pharmaceutically acceptable salt of the purine derivative or the tautomer to treat or prevent an allergic disease.

6. A method of regulating an immune response in a subject in need thereof, comprising administering to the subject a composition comprising a purine derivative represented by General Formula (I)

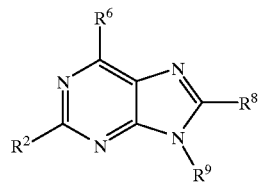
(I)

wherein

R$^2$ is hydrogen or a C$_{1-14}$ hydrocarbon in which —CH$_2$— not directly bound to the purine skeleton and CH$_2$ in —CH$_3$ not directly bound to the purine skeleton may be substituted by carbonyl, sulfonyl, —O— or —S—; =CH$_2$ may be substituted by =O or =S; C—H in —CH$_2$— not directly bound to the purine skeleton, C—H in —CH$_3$ not directly bound to the purine skeleton, C—H in >CH— not directly bound to the purine skeleton, C—H in =CH— not directly bound to the purine skelton and C—H in =CH$_2$ may be substituted by N, C-halogen or C—CN;

R$^6$ is hydroxyl, amino or amino which is mono- or di-substituted by a C$_{1-10}$ hydrocarbon group(s);

R$^8$ is hydroxyl, mercapto, C$_{1-18}$ acyloxy or C$_{1-19}$ hydrocarbon group-substituting oxycarbonyloxy; and R$^9$ is a C$_{1-14}$ hydrocarbon group in which —CH$_2$— not directly bound to the purine skeleton and CH$_2$ in —CH$_3$ not directly bound to the purine skeleton may be substituted by carbonyl, sulfonyl, —O— or —S—; =CH$_2$ may be substituted by =O or =S; C—H in —CH$_2$— not directly bound to the purine skeleton, C—H in —CH$_3$ not directly bound to the purine skeleton, C—H in >CH— not directly bound to the purine skeleton, C—H in =CH— not directly bound to the purine skeleton, C—H in =CH$_2$ and C—H in ≡CH may be substituted by N, C-halogen or C—CN;

or its tautomer or a pharmaceutically acceptable salt of the purine derivative or the tautomer to regulate an immune response.

* * * * *